US011077110B2

(12) United States Patent
Hu

(10) Patent No.: US 11,077,110 B2
(45) Date of Patent: Aug. 3, 2021

(54) COMPOSITIONS AND METHODS FOR TREATING AND PREVENTING METABOLIC DISORDERS

(71) Applicant: TUFTS MEDICAL CENTER, Boston, MA (US)

(72) Inventor: Miaofen G. Hu, Boston, MA (US)

(73) Assignee: Tufts Medical Center, Boston, MA (US)

( * ) Notice: Subject to any disclaimer, the term of this patent is extended or adjusted under 35 U.S.C. 154(b) by 18 days.

(21) Appl. No.: 16/086,143

(22) PCT Filed: Mar. 17, 2017

(86) PCT No.: PCT/US2017/022944
§ 371 (c)(1),
(2) Date: Sep. 18, 2018

(87) PCT Pub. No.: WO2017/161253
PCT Pub. Date: Sep. 21, 2017

(65) Prior Publication Data
US 2019/0192518 A1    Jun. 27, 2019

Related U.S. Application Data

(60) Provisional application No. 62/310,347, filed on Mar. 18, 2016.

(51) Int. Cl.
| | | |
|---|---|---|
| A61K 31/519 | (2006.01) | |
| A61P 3/04 | (2006.01) | |
| A61K 31/506 | (2006.01) | |
| A61K 45/06 | (2006.01) | |
| A01K 67/027 | (2006.01) | |
| C12N 15/113 | (2010.01) | |

(52) U.S. Cl.
CPC ........ *A61K 31/519* (2013.01); *A01K 67/0276* (2013.01); *A01K 67/0278* (2013.01); *A61K 31/506* (2013.01); *A61K 45/06* (2013.01); *A61P 3/04* (2018.01); *C12N 15/1135* (2013.01); *C12Y 207/11022* (2013.01); *A01K 2217/072* (2013.01); *A01K 2217/15* (2013.01); *A01K 2217/206* (2013.01); *A01K 2227/105* (2013.01); *A01K 2267/0362* (2013.01); *C12N 2310/14* (2013.01); *C12N 2310/531* (2013.01); *C12N 2740/16043* (2013.01); *C12N 2740/16052* (2013.01); *C12N 2800/30* (2013.01)

(58) Field of Classification Search
CPC .... A61K 31/519; A61K 31/506; A61K 45/06; A01K 67/0276; A01K 2217/072; A01K 2217/15; A01K 2217/206; A01K 2267/0362

USPC .................................................... 514/252.16
See application file for complete search history.

(56) References Cited

U.S. PATENT DOCUMENTS

| | | |
|---|---|---|
| 9,259,399 B2 | 2/2016 | Chen-Kiang et al. |
| 2003/0004351 A1 | 1/2003 | Davis et al. |
| 2003/0229026 A1 | 12/2003 | Rima Salim et al. |
| 2004/0006074 A1 | 1/2004 | Kelley et al. |
| 2004/0048915 A1 | 3/2004 | Albert et al. |
| 2007/0027147 A1 | 2/2007 | Takashi et al. |
| 2007/0179118 A1 | 8/2007 | Mark et al. |
| 2010/0160340 A1 | 6/2010 | Coates et al. |
| 2010/0298314 A1 | 11/2010 | Reddy et al. |
| 2011/0274616 A1 | 11/2011 | Wyatt et al. |
| 2013/0065886 A1 | 3/2013 | Pastor Fernandez et al. |
| 2013/0184285 A1 | 7/2013 | Thomas et al. |
| 2014/0271466 A1* | 9/2014 | Sharpless ................ A61P 35/04 424/1.65 |
| 2014/0350244 A1 | 11/2014 | Connors et al. |

FOREIGN PATENT DOCUMENTS

| | | |
|---|---|---|
| WO | WO 2011/101409 | 8/2011 |
| WO | WO 2011/101417 | 8/2011 |
| WO | WO 2014/183520 | 11/2014 |
| WO | WO 2015/101293 | 7/2015 |
| WO | WO 2015/180642 | 12/2015 |
| WO | WO 2016/014904 | 1/2016 |
| WO | WO 2016/015597 | 2/2016 |
| WO | WO 2016/040848 | 3/2016 |
| WO | WO 2017/161253 | 9/2017 |

OTHER PUBLICATIONS

Senderowicz et al., Journal of clinical Oncology, 1998, 16(9), 2986-2999 (Year: 1998).*
Pharmacy and Theraputics, 2015, 40(3) p. 152 (Year: 2015).*
International Search Report of related PCT/US2017/022944, dated Jun. 6, 2017, 5 pages.
Written Opinion of related PCT/US2017/022944, dated Jun. 6, 2017, 7 pages.

(Continued)

*Primary Examiner* — Yevgeny Valenrod
(74) *Attorney, Agent, or Firm* — Casimir Jones, S.C.; Tanya A. Arenson

(57) ABSTRACT

Provided herein are compositions and methods for treating or preventing metabolic disorders. In particular, provided herein are compositions, methods, and uses of Cyclin-dependent Kinase 6 (CDK6) inhibitors for treating and preventing metabolic diseases (e.g., type II diabetes, obesity, metabolic syndrome, elevated blood pressure, cardiovascular diseases, elevated fasting plasma glucose, and high serum triglycerides).

11 Claims, 23 Drawing Sheets
Specification includes a Sequence Listing.

(56) References Cited

OTHER PUBLICATIONS

Aune et al., "Isolation and differentiation of stromal vascular cells to beige/brite cells." J Vis Exp. Mar. 28, 2013;(73), 1-6.
Bi et al., "Inhibition of Notch signaling promotes browning of white adipose tissue and ameliorates obesity." Nat Med. Aug. 2014;20(8):911-8.
Biggs et al., "AML1/RUNX1 phosphorylation by cyclin-dependent kinases regulates the degradation of AML1/RUNX1 by the anaphase-promoting complex." Mol Cell Biol. Oct. 2006;26(20):7420-9.
Bunnell et al., "Differentiation of Adipose Stem Cells" Methods in Molecular Biology vol. 456, 2008, Adipose Tissue Protocols pp. 155-171.
Butler et al. "A Recurring Problem With the Analysis of Energy Expenditure in Genetic Models Expressing Lean and Obese Phenotypes" Diabetes. Feb. 2010; 59(2): 323-329.
Cederberg et al., "FOXC2 Is a Winged Helix Gene that Counteracts Obesity, Hypertriglyceridemia, and Diet-Induced Insulin Resistance" Cell, vol. 106, Issue 5, Sep. 7, 2001, pp. 563-573.
Chen et al., "Runx1 is required for the endothelial to hematopoietic cell transition but not thereafter" Nature. Feb. 12, 2009; 457(7231): 887-891.
Cristancho et al., "Forming functional fat: a growing understanding of adipocyte differentiation" Nature reviews Molecular cell biology 12.11 (2011): 722-34.
Cypess et al., "Identification and importance of brown adipose tissue in adult humans." N Engl J Med. Apr. 9, 2009;360(15):1509-17.
Frost et al. "Control of glucose homeostasis and insulin sensitivity by the Let-7 family of microRNAs."Proc Natl Acad Sci U S A. Dec. 27, 2011;108(52):21075-80.
Fry et al., "Specific inhibition of cyclin-dependent kinase 4/6 by PD 0332991 and associated antitumor activity in human tumor xenografts." Molecular cancer therapeutics 3, No. 11 (2004): 1427-1438.
Fujimoto et al., "Cdk6 blocks myeloid differentiation by interfering with Runx1 DNA binding and Runx1-C/EBPα interaction" EMBO J. May 2, 2007; 26(9): 2361-2370.
Hansen et al., "Activation of peroxisome proliferator-activated receptor γ bypasses the function of the retinoblastoma protein in adipocyte differentiation." Journal of Biological Chemistry 274.4 (1999): 2386-2393.
Hu et al., "A requirement for cyclin-dependent kinase 6 in thymocyte development and tumorigenesis." Cancer Res. Feb. 1, 2009;69(3):810-8.
Hu et al., "CDK6 kinase activity is required for thymocyte development." Blood. Jun. 9, 2011;117(23):6120-31.
Ichikawa et al., "AML-1 is required for megakaryocytic maturation and lymphocytic differentiation, but not for maintenance of hematopoietic stem cells in adult hematopoiesis." Nat Med. Mar. 2004;10(3):299-304.
Kintscher et al., "T-lymphocyte infiltration in visceral adipose tissue: a primary event in adipose tissue inflammation and the development of obesity-mediated insulin resistance." Arterioscler Thromb Vasc Biol. Jul. 2008;28(7):1304-10.
Kohrt et al., "CDK6 binds and promotes the degradation of the EYA2 protein." Cell Cycle. 2014;13(1):62-71.
Kozar et al., "Cell cycle progression without cyclin D-CDK4 and cyclin D-CDK6 complexes." Cell Cycle. Mar. 2005;4(3):388-91.
Lafontan et al., "Fat cell adrenergic receptors and the control of white and brown fat cell function." J Lipid Res. Jul. 1993;34(7):1057-91.
Lee et al., "Lessons on conditional gene targeting in mouse adipose tissue." Diabetes. Mar. 2013;62(3):864-74.
Lowell et al., "Towards a molecular understanding of adaptive thermogenesis." Nature. Apr. 6, 2000;404(6778):652-60.
Park et al., "Inhibition of STAT3 activity delays obesity-induced thyroid carcinogenesis in a mouse model." Endocr Relat Cancer. Jan. 2016;23(1):53-63.
Pavletich "Mechanisms of cyclin-dependent kinase regulation: structures of Cdks, their cyclin activators, and Cip and INK4 inhibitors." J Mol Biol. Apr. 16, 1999;287(5):821-8.
Picard et al., "SRC-1 and TIF2 control energy balance between white and brown adipose tissues." Cell. Dec. 27, 2002;111(7):931-41.
Pikman et al., "Synergistic Drug Combinations with a CDK4/6 Inhibitor in T-cell Acute Lymphoblastic Leukemia." Clin Cancer Res. Feb. 15, 2017;23(4):1012-1024.
Puigserver et al., "A cold-inducible coactivator of nuclear receptors linked to adaptive thermogenesis." Cell. Mar. 20, 1998;92(6):829-39.
Rader et al., "Dual CDK4/CDK6 inhibition induces cell-cycle arrest and senescence in neuroblastoma." Clin Cancer Res. Nov. 15, 2013;19(22):6173-82.
Rausch et al., "Obesity in C57BL/6J mice is characterized by adipose tissue hypoxia and cytotoxic T-cell infiltration." Int J Obes (Lond). Mar. 2008;32(3):451-63.
Rosen et al., "Transcriptional regulation of adipogenesis." Genes Dev. Jun. 1, 2000;14(11):1293-307.
Saltiel "New perspectives into the molecular pathogenesis and treatment of type 2 diabetes." Cell. Feb. 23, 2001;104(4):517-29.
Seale et al., "Prdm16 determines the thermogenic program of subcutaneous white adipose tissue in mice." J Clin Invest. Jan. 2011;121(1):96-105.
Sera et al., "Hematopoietic stem cell origin of adipocytes." Exp Hematol. Sep. 2009;37(9):1108-20.
Sherr et al., "Inhibitors of mammalian G1 cyclin-dependent kinases." Genes Dev. May 15, 1995;9(10):1149-63.
Van Marken Lichtenbelt et al., "Cold-activated brown adipose tissue in healthy men."N Engl J Med. Apr. 9, 2009;360(15):1500-8.
Wan et al., "Loss of Akt1 in mice increases energy expenditure and protects against diet-induced obesity." Mol Cell Biol. Jan. 2012;32(1):96-106.
Wu et al., "T-cell accumulation and regulated on activation, normal T cell expressed and secreted upregulation in adipose tissue in obesity." Circulation. Feb. 27, 2007;115(8):1029-38.
Wu et al., "Beige adipocytes are a distinct type of thermogenic fat cell in mouse and human." Cell. Jul. 20, 2012;150(2):366-76.

\* cited by examiner

Figure 9

(SEQ ID NO:1)

```
   1 aacctctccg cgcgaagacg gcttcagccc tgcagggaaa gaaaagtgca atgattctgg
  61 actgagacgc gcttgggcag aggctatgta atcgtgtctg tgttgaggac ttcgcttcga
 121 ggagggaaga ggagggatcg gctcgctcct ccggcggcgg cggcggcggc gactctgcag
 181 gcggagtttc gcggcggcgg caccaggggtt acgccagccc cgcggggagg tctctccatc
 241 cagcttctgc agcggcgaaa gccccagcgc ccgagcgcct gagccggcgg ggagcaagta
 301 aagctagacc gatctccggg gagccccgga gtaggcgagc ggcggccgcc agctagttga
 361 gcgcaccccc cgcccgcccc agcggcgccg cggcgggcgg cgtccaggcg gcatggagaa
 421 ggacggcctg tgccgcgctg accagcagta cgaatgcgtg gcggagatcg ggagggcgc
 481 ctatgggaag gtgttcaagg cccgcgactt gaagaacgga ggccgtttcg tggcgttgaa
 541 gcgcgtgcgg gtgcagaccg gcgaggaggg catgccgctc tccaccatcc gcgaggtggc
 601 ggtgctgagg cacctggaga ccttcgagca ccccaacgtg gtcaggttgt ttgatgtgtg
 661 cacagtgtca cgaacagaca gagaaaccaa actaacttta gtgtttgaac atgtcgatca
 721 agacttgacc acttacttgg ataaagttcc agagcctgga gtgcccactg aaaccataaa
 781 ggatatgatg tttcagcttc tccgaggtct ggactttctt cattcacacc gagtagtgca
 841 tcgcgatcta aaaccacaga acattctggt gaccagcagc ggacaaataa aactcgctga
 901 cttcggcctt gcccgcatct atagtttcca gatggctcta acctcagtgg tcgtcacgct
 961 gtggtacaga gcacccgaag tcttgctcca gtccagctac gccaccccccg tggatctctg
1021 gagtgttggc tgcatatttg cagaaatgtt tcgtagaaag cctcttttc gtggaagttc
1081 agatgttgat caactaggaa aaatcttgga cgtgattgga ctcccaggag aagaagactg
1141 gcctagagat gttgcccttc ccaggcaggc ttttcattca aaatctgccc aaccaattga
1201 gaagtttgta acagatatcg atgaactagg caaagaccta cttctgaagt gtttgacatt
1261 taacccagcc aaaagaatat ctgcctacag tgccctgtct cacccatact tccaggacct
1321 ggaaaggtgc aaagaaaacc tggattccca cctgccgccc agccagaaca cctcggagct
1381 gaatacagcc tgaggcctca gcagccgcct taagctgatc ctgcggagaa caccccttggt
1441 ggcttatggg tcccctcag caagccctac agagctgtgg aggattgcta tctggaggcc
1501 ttccagctgc tgtcttctgg acaggctctg cttctccaag gaaaccgcct agtttactgt
1561 tttgaaatca atgcaagagt gattgcagct ttatgttcat tgtttgttt gtttgtctgt
1621 ttgtttcaag aacctggaaa aattccagaa gaagagaagc tgctgaccaa ttgtgctgcc
1681 atttgatttt tctaaccttg aatgctgcca gtgtggagtg ggtaatccag gcacagctga
1741 gttatgatgt aatctctctg cagctgcgg gcctgatttg gtacttttga gtgtgtgtgt
1801 gcatgtgtgt gtgtgtgtgt gtgtgtgtgt gtgtgtatgt gagagattct gtgatctttt
1861 aaagtgttac ttttttgtaaa cgacaagaat aattcaattt taaagactca aggtggtcag
1921 taaataacag gcatttgttc actgaaggtg attcaccaaa atagtcttct caaattagaa
1981 agttaacccc atgtcctcag catttctttt ctggccaaaa gcagtaaatt tgctagcagt
2041 aaaagatgaa gttttataca cacagcaaaa aggagaaaaa attctagtat attttaagag
2101 atgtgcatgc attctattta gtcttcagaa tgctgaattt acttgttgta agtctatttt
2161 aaccttctgt atgacatcat gctttatcat ttcttttgga aaatagcctg taagcttttt
2221 attacttgct ataggtttag ggagtgtacc tcagatagat tttaaaaaaa agaatagaaa
2281 gcctttattt cctggtttga aattcctttc ttcccttttt tgttgttgt tattgttgtt
2341 tgttgttgtt attttgtttt tgttttaggg aatttgtcag aaactctttc ctgttttggt
2401 ttggagagta gttctctcta actagagaca ggagtggcct tgaaattttc ctcatctatt
2461 acactgtact ttctgccaca cactgccttg ttggcaaagt atccatcttg tctatctccc
2521 ggcacttctg aaatatattg ctaccattgt ataactaata acagattgct taagctgttc
2581 ccatgcacca cctgtttgct tgctttcaat gaacctttca taaattcgca gtctcagctt
2641 atggtttatg gcctcgattc tgcaaaccta acagggtcac atatgttctc taatgcagtc
2701 cttctacctg gtgtttactt ttgttaccta aataatgagt aggatcttgt tttgttttat
2761 caccagcaca cagattgcta taaactgtta ctttgtgaat tacatttta tagaagatat
2821 tttcagtgtc tttacctgag ggtatgtctt tagctatgtt ttagggccat acatttactc
2881 tatcaaatga tcttttctcc atcccccagg ctgtgcttat ttctagtgcc ttgtgctcac
2941 tcctgctctc tacagagcca gcctggcctg gcattgtaa acagcttttc ctttttctct
3001 tactgttttc tctacagtcc tttatatttc ataccatctc tgccttataa gtggtttagt
3061 gctcagttgg ctctagtaac cagaggacac agaaagtatc ttttggaaag tttagccacc
3121 tgtgctttct gactcagagt gcatgcaaca gttagatcat gcaacagtta gattatgttt
3181 agggttagga ttttcaaaga atggaggttg ctgcactcag aaaataattc agatcatgtt
3241 tatgcattat taagttgtac tgaattcttt gcagcttaat gtgatatatg actatcttga
3301 acaagagaaa aaactaggag atgtttctcc tgaagagctt tgggggttgg gaactattct
3361 ttttttaattg ctgtactact taacattgtt ctaattcagt agcttgagga acaggaacat
```

Figure 9 (cont.)

```
3421 tgttttctag agcaagataa taaaggagat gggccataca aatgttttct actttcgttg
3481 tgacaacatt gattaggtgt tgtcagtact ataaatgctt gagatataat gaatccacag
3541 cattcaaggt caggtctact caaagtctca catggaaaag tgagttctgc ctttcctttg
3601 atcgagggtc aaaatacaaa gacatttttg ctagggccta caaattgaat ttaaaaactc
3661 actgcactga ttcatctgag ctttttggtt agtattcatg gctagagtga acatagcttt
3721 agttttgct gttgtaaaag tgttttcata agttcactca agaaaaatgc agctgttctg
3781 aactggaatt tttcagcatt ctttagaatt ttaaatgagt agagagctca acttttattc
3841 ctagcatctg cttttgactc atttctaggc agtgcttatg aagaaaaatt aaagcacaaa
3901 cattctggca ttcaatcgtt ggcagattat cttctgatga cacagaatga aagggcatct
3961 cagcctctct gaactttgta aaaatctgtc cccagttctt ccatcggtgt agttgttgca
4021 tttgagtgaa tactctcttg atttatgtat tttatgtcca gattcgccat ttctgaaatc
4081 cagatccaac acaagcagtc ttgccgttag ggcattttga agcagatagt agagtaagaa
4141 cttagtgact acagcttatt cttctgtaac atatggtttc aaacatcttt gccaaaagct
4201 aagcagtggt gaactgaaaa gggcatattg ccccaaggtt acactgaagc agctcatagc
4261 aagttaaaat attgtgacag atttgaaatc atgtttgaat ttcatagtag gaccagtaca
4321 agaatgtccc tgctagtttc tgtttgatgt ttggttctgg cggctcaggc attttgggaa
4381 ctgttgcaca gggtggagtc aaaacaacct acatataaaa agagaaaaag agaaacttgt
4441 ccatttagct ttcataagaa atcccatggc aaagggtaat aaaaaggacc taatcttaaa
4501 aatacaattt ctaagcactt gtaagaaccc agtgggttgg agcctcccac tttgtccctc
4561 ctttgaagtg gatgggaact caaggtgcaa agaacctgtt ttggaagaaa gcttggggcc
4621 atttcagccc cctgtattct catgattttc tctcaggaag cacacactgt gaatggcaga
4681 cttttcattt agccccaggt gacttactaa aaatagttga aaattattca cctaagaata
4741 gaatctcagc attgtgttaa ataaaaatga agctttaga aggcatgaga tgttcctatc
4801 ttaaataaag catgtttctt ttctatagag aaatgtatag tttgactctc cagaatgtac
4861 tatccatctt gatgagaaaa ctcttaaata gtaccaaaca ttttgaactt taaattatgt
4921 atttaaagtg agtgtttaag aaactgtagc tgcttctttt acaagtggtg cctattaaag
4981 tcagtaatgg ccattattgt tccattgtgg aaattaaatt atgtaagctt cctaatatca
5041 taaacatatt aaaattcttc taaaatattg cttttctttt aagtgacaat ttgactattc
5101 ttatgataag cacatgagag tgtcttacat tttccaaaag caggcttta ttgcatagtt
5161 gagtctagga aaaataatg ttaaagtga atatgccacc ataattactt aattatgtta
5221 gtatagaaac tacagaatat ttaccctgga aagaaaatat tggaatgtta ttataaactc
5281 ttagatattt atataattca aaagaatgca tgtttcacat tgtgacagat aaagatgtat
5341 gatttctaag gctttaaaaa ttattcataa aacagtgggc aatagataaa ggaaattctg
5401 gagaaaatga aggtatttaa agggtagttt caaagctata tatattttga aggatatatt
5461 ctttatgaac aaatatattg taaaaattta tactaaggtc atctggtaac tgtgggatta
5521 atatggtcga aaacaaatgt tatggagaag ctgtcccaag caaactaaat tacctgtact
5581 tttttcccat ttcaagggaa gaggcaacca catgaagcaa tacttcttac acatgcctaa
5641 gaacgttcat tgaaaaaata aattttttaaa aggcatgtgt ttcctatgcc accaatactt
5701 ttgaaaaatt gtgaacctta cccaaaacca tttatcatgt ccattaagta tatttgggta
5761 tataattagg aagatattta catgttccat ctccacagtg gaaaaactta ttgaggctac
5821 caaagtgtgc caagaaatgt aagtccttag agtaattaga aatgctgttt tcctcaaaag
5881 catgagaaac tagcattttc atttcttatt tactcccttt ctatatcaat gcaattcaca
5941 acccaattttt aatacatccc tatatctcaa gcatttctat cttgtacttt ttcagaaaat
6001 aaaccaaaaa taatcctttg gtctctctat cttctgacct ttgtaagcaa cagaaatgta
6061 aaaacagaag gggtccaatt tttacacgtt tttttctcaa gtagcctttc tggggatttt
6121 tattttctta atgaagtgcc aatcagcttt tcaaaatgtt ttctatttct cagcatttcc
6181 aggaagtgat aacgtttagc taaatgagta gaagtggact tccttcaaca tattgttacc
6241 ttgtctagcc ttaggaagaa aacaagagcc acctgaaaat aaaatacaggc tcttttcgag
6301 catctgctga aatactgtta cagcaatttg aagttgatgt ggtaggaaag gaaggtgact
6361 tttcttgcaa aagtcttttct aaacattcac actgtcctaa gagatgagct ttcttgtttt
6421 attccggtat attccacaag gtggcacttt tagagaaaaa caaatctgat gaagactaaa
6481 gaggtacttc taaaagagat ttcattctaa ctttattttt ctgcgcatat ttaactcttt
6541 cctagcactt gttttttggg atgattaata gtctctataa tgttctgtaa cttcaatatt
6601 ttacttgtta cctaggttct gaacaattgt ctgcaaataa attgttctta aggatggata
6661 atacacccat tttgatcatt taagtaaaga aagcctagtc attcattcag tcaagaaaaa
6721 attttgaag tacccagtta ccttactttt ctagattaaa acaggcttag ttactaaaaa
6781 ggcagtcctc atctgtgaac aggatagttt cgttagaagt ataaaactcc tttagtggcc
```

Figure 9 (cont.)

```
 6841 ccagttaaaa cacacatacc ctctctgctg ctttcaaatt ccctagcatg gtggcctttc
 6901 aacattgatt aaattttaaa atcctaattt aaagatcagg tgagcaaaat gagtagcaca
 6961 tcagtaattc agtagacaaa acttttgtct gaaaaattgc tgtattgaaa cagagcccta
 7021 aaataccaaa agaccaggta attttaacat ttgtggaatc acaaatgtaa attcataaga
 7081 agctctaatt aaaaaaaaaa agtctgaagt atatgagcat aacaacttag gagtgtgtct
 7141 acatacttaa cttttgaagt tttttggcaa ctttatatac ttttttttaaa tttacaagtc
 7201 tacttaaaga cttcttatac cccaaatgat taagttaatt ttagaggtca ccttttctcac
 7261 agcagtgtca cttgaaattt agtagggaag gatattgcag tatttttcag tttccttagc
 7321 acagcaccac agaaagcagc ttattccttt tgagtggcag acactcgacg gtgcctgccc
 7381 aactttcctc ctgagtggca agcagatgag tctcagtaat tcatactgaa ccaaaatgcc
 7441 acatacacta ggggcagtca gaaactggct gagaaatccc ccgcctcatt cgcccctctg
 7501 ctcccaggaa ctagagtcca gttaaagccc ctatgcgaaa ggccgaattc caccccaggg
 7561 tttgttataa cagtggccag tctgaacccc atttgctcgt gctcaaaact tgattcccac
 7621 ttgaaagcct tccgggcgcg ctgcctcgtt gccccgcccc tttggcagga gagaggcagt
 7681 gggcgaggcc gggctgggc cccgcctccc actcacctgc cggtgcctga aattatgtgc
 7741 ggccccgcgg gctgctttcc gaggtcagag tgccctgctg ctgtctcaga ggcatctgtt
 7801 ctgcaaatct taggaagaaa aatgtcccta gtagcaaacg ggtgtcttct gtgcataaat
 7861 aagtacaaca caattctccg aaagttcggg taaaagaga tgcggtagca gctgccctgt
 7921 gtgaagctgt ctaccccgca tctctcaggc gctaagctca gttttgttt ttgttttgt
 7981 ttttttaaag aaaagatgta taattgcagg aattttttt tattttttta ttttccatca
 8041 ttctatatat gtgatggtga aagatatgcc tggaaaagtt ttgttttgaa aagtttattt
 8101 tctgcttcgt cttcagttgg caaaagctct caattcttta gcttccagtt tcttttctct
 8161 cttttctttt gttaggtaat taaaggtatg taaacaaatt atctcatgta gcagggatt
 8221 ttcatgttga gaggaatctt ccgtgtgagt tgtttggtca cacaaataac cctttctcaa
 8281 ttttaggagt ttggattgtc aaatgtaggt ttttctcaaa gggggcatat aactacatat
 8341 tgactgccaa gaactatgac tgtagcacta atcagcacac atagagccac acaattattt
 8401 aatttctaac tctctgtggt ccctagaaaa attccgttga tgtgcttagg ttaaagttct
 8461 gaagataccc gttgtaccct tacttgaaag tttctaatct taagttttat gaaatgcaat
 8521 aatatgtatc agctagcaat atttctgtga tcaccaacaa ctctcagttt gatcttaaag
 8581 tctgaataat aaaacaaatc ccagcagtaa tacatttctt aaacctcaca gtgcatgata
 8641 tatcttttca ttctgatcct gtgtttgcaa aaatatacac atgtatatca tagttcctca
 8701 cttttttattc atttgttttc ctattacctg tagtaaatat attagttagt acatggaatt
 8761 tatagcatca gctaccccca ggaacagcac ctgacaggcg gggatttt tttcaagttg
 8821 ttctacattt gcataaatta tttctattat tattcatgta tgttatttat ttctgaatca
 8881 cactagtcct gtgaaagtac aactgaaggc agaaagtgtt aggattttgc atctaatgtt
 8941 cattatcatg gtattgatgg acctaagaaa ataaaaatta gactaagccc ccaaataagc
 9001 tgcatgcatt tgtaacatga ttagtagatt tgaatatata gatgtagtat tttgggtatc
 9061 taggtgtttt atcattatgt aaaggaatta aagtaaagga ctttgtagtt gttttttatta
 9121 aatatgcata tagtagagtg caaaaatata gcaaaaataa aaactaaagg tagaaaagca
 9181 ttttagatat gccttaattt agaaactgtg ccaggtggcc ctcggaatag atgccaggca
 9241 gagaccagtg cctgggtggt gcctcctctt gtctgccctc atgaagaagc ttccctcacg
 9301 tgatgtagtg ccctcgtagg tgtcatgtgg agtagtggga acaggcagta ctgttgagag
 9361 gagagcagtg tgagagtttt tctgtagaag cagaactgtc agcttgtgcc ttgaggcttc
 9421 cagaacgtgt cagatggaga agtccaagtt tccatgcttc aggcaactta gctgtgtaca
 9481 gaagcaatcc agtgtggtaa taaaaagcaa ggattgcctg tataatttat tataaaataa
 9541 aagggatttt aacaaccaac aattcccaac acctcaaaag cttgttgcat tttttggtat
 9601 ttgaggtttt tatctgaagg ttaaagggca agtgtttggt atagaagagc agtatgtgtt
 9661 aagaaaagaa aaatattggt tcacgtagag tgcaaattag aactagaaag ttttatacga
 9721 ttatcatttt gagatgtgtt aaagtaggtt ttcactgtaa aatgtattag tgtttctgca
 9781 ttgccatagg gcctggttaa aactttctct taggtttcag gaagactgtc acatacagta
 9841 agctttttc cttctgactt ataatagaaa atgttttgaa agtaaaaaaa aaaatctaa
 9901 tttggaaatt tgacttgtta gtttctgtgt ttgaaatcat ggttctagaa atgtagaaat
 9961 tgtgtatatc agatactcat ctaggctgtg tgaaccagcc caagatgacc aacatcccca
10021 cacctctaca tctctgtccc ctgtatctct tcctttctac cactaaagtg ttccctgcta
10081 ccatcctggc ttgtccacat ggtgctctcc atcttcctcc acatcatgga ccacaggtgt
10141 gcctgtctag gcctggccac cactcccaac ttgacctagc cacattcatc tagagatggt
10201 tcctgatgct gggcacagac tgtgctcatg gcacccatta gaaatgcctc tagcatcttt
```

Figure 9 (cont.)

```
10261 gtatgcatct tgatttttaa accaagtcat tgtacagagc attcagtttt ggctgtggta
10321 ccaagagaaa aactaatcaa gaatataaac cacattccag gctgctgttt tctctccatc
10381 tacaggccac acttttactg tatttcttca tacttgaaat tcattctgct attttcatat
10441 cagggtacag acttataagg gtgcatgttc cttaaaggtg cataattatt cttattccgt
10501 ttgcttatat tgctacagaa tgctctgttt tggtgctttg agttctgcag acccaagaag
10561 cagtgtggaa attcactgcc tgggacacag tcttataaga atgttggcag gtgactttgt
10621 atcagatgtt gcttctcttt tctctgtaca cagattgaga gttaccacag tggcctgtcg
10681 ggtccaccct gtgggtgcag cacagctctc tgaaagcaag aaccttccta cctattctaa
10741 cgttttttgcc ctctaagaaa aatggcctca ggtatggtat agacatagca agaggggaag
10801 ggctgtctca ctctagcaac catccctcca ttacacacag aaagccctct tgaagcaaaa
10861 gaagaagaaa gaaagaaagc ttatctctaa ggctactgtc ttcagaatgc tctgagctga
10921 atgctcttgc tcctttccca agaggcagat gaaaatatag ccagtttatc tataccttc
10981 ctatctgagg aggagaatag aaaagtaggg taaatatgta acgtaaaata tgtcattcaa
11041 ggaccaccaa aactttaagt accctatcat taaaaatctg gttttaaaag tagctcaagt
11101 aagggatgct ttgtgaccca gggtttctga agtcagatag ccattcttac ctgcccctta
11161 ctctgactta ttgggaaagg gagaactgca gtggtgtttc tgttgcagtg gcaaaggtaa
11221 catgtcagaa aattcagagg gttgcatacc aataatcctt tggaaactgg atgtcttact
11281 gggtgctaga atgaaaatgt aggtatttat tgtcagatga tgaagttcat tgttttttc
11341 aaaattggtg ttgaaatatc actgtccaat gtgttcactt atgtgaaagc taaattgaat
11401 gaggcaaaaa gagcaaatag tttgtatatt tgtaatacct tttgtatttc ttacaataaa
11461 aatattggta gcaaataaaa ataataaaaa caataacttt aaactgcttt ctggagatga
11521 attactctcc tggctatttt cttttttact ttaatgtaaa atgagtataa ctgtagtgag
11581 taaaattcat taaattccaa gttttagcag aaaaaaaaaa aaaaaaaa
```

COMPOSITIONS AND METHODS FOR TREATING AND PREVENTING METABOLIC DISORDERS

This application is a 371 U.S. National Phase Entry of pending International Application No. PCT/US2017/022944, filed Mar. 17, 2017, which claims priority to U.S. Provisional Patent Application Ser. No. 62/310,347, filed Mar. 18, 2016, which are herein incorporated by reference in their entireties.

FIELD

Provided herein are compositions and method for treating or preventing metabolic disorders. In particular, provided herein are compositions, methods, and uses of CDK6 inhibitors for treating and preventing metabolic diseases (e.g., diabetes, obesity, and cardiovascular disease).

BACKGROUND

Diabetes mellitus type 2 is a long term metabolic disorder that is characterized by high blood sugar, insulin resistance, and relative lack of insulin. Common symptoms include increased thirst, frequent urination, and unexplained weight loss. Symptoms may also include increased hunger, feeling tired, and sores that do not heal. Often symptoms come on slowly. Long-term complications from high blood sugar include heart disease, strokes, diabetic retinopathy which can result in blindness, kidney failure, and poor blood flow in the limbs which may lead to amputations. The sudden onset of hyperosmolar hyperglycemic state may occur; however, ketoacidosis is uncommon.

Type 2 diabetes is primarily due to obesity and not enough exercise in people who are genetically predisposed. It makes up about 90% of cases of diabetes, with the other 10% due primarily to diabetes mellitus type 1 and gestational diabetes. Diagnosis of diabetes is by blood tests such as fasting plasma glucose, oral glucose tolerance test, or A1C.

Type 2 diabetes is partly preventable by staying a normal weight, exercising regularly, and eating properly. Treatment involves exercise and dietary changes. If blood sugar levels are not adequately lowered, the medication metformin is typically recommended. Many people may eventually also require insulin injections. In those on insulin, routinely check blood sugar levels is advised, however this may not be needed in those taking pills. Bariatric surgery often improves diabetes in those who are obese.

Rates of type 2 diabetes have increased markedly since 1960 in parallel with obesity. As of 2013 there were approximately 368 million people diagnosed with the disease compared to around 30 million in 1985. Typically it begins in middle or older age. Type 2 diabetes is associated with a ten-year-shorter life expectancy.

New treatments for diabetes and associated conditions are needed.

SUMMARY

Provided herein are compositions and method for treating or preventing metabolic disorders. In particular, provided herein are compositions, methods, and uses of CDK6 inhibitors for treating and preventing metabolic diseases (e.g., diabetes, obesity, and cardiovascular disease).

In some embodiments, the present disclosure provides a method of treating or preventing metabolic disease in a subject, comprising: administering a CDK6 inhibitor to the subject. The present disclosure is not limited to particular CDK6 inhibitors. Examples include, but are not limited to, a nucleic acid (e.g., siRNA, miRNA, antisense nucleic acid, shRNA, etc.), a small molecule (e.g., PD0332991, LEE011, flavopiridol, AT7519, JNJ-7706621, or P276-00), or an antibody. In some embodiments, the wherein the CDK4/6 inhibitor is selected from those described in the publications listed in: US20070027147; US20030229026; US 20040048915; US20040006074; US20070179118; WO2016040848; WO2016015597; WO2016014904; WO2015/180642; WO2015101293; US20140350244; WO2014183520; WO2011101409; WO2011101417; US20130184285; US 20100160340, each of which is incorporated by reference herein in its entirety. The present disclosure is not limited to particular metabolic diseases. Examples include, but are not limited to, type II diabetes, obesity, metabolic syndrome, elevated blood pressure, elevated fasting plasma glucose, or high serum triglycerides. In some embodiments, the administering converts white fat to brown fat in the subject. In some embodiments, the subject is or is not overweight or obese. In some embodiments, the subject exhibits or does not exhibit symptoms of the metabolic disease.

Further embodiments provide the use of a CDK6 inhibitor to treat or prevent a metabolic disease in a subject in need thereof.

In some embodiments, the CDK6 inhibitor is administered in combination with a second agent that treats a metabolic disease.

Additional embodiments are described herein.

DESCRIPTION OF THE FIGURES

FIG. 9 shows the sequence of CDK6 mRNA (SEQ ID NO: 1).

DEFINITIONS

Figure 1:
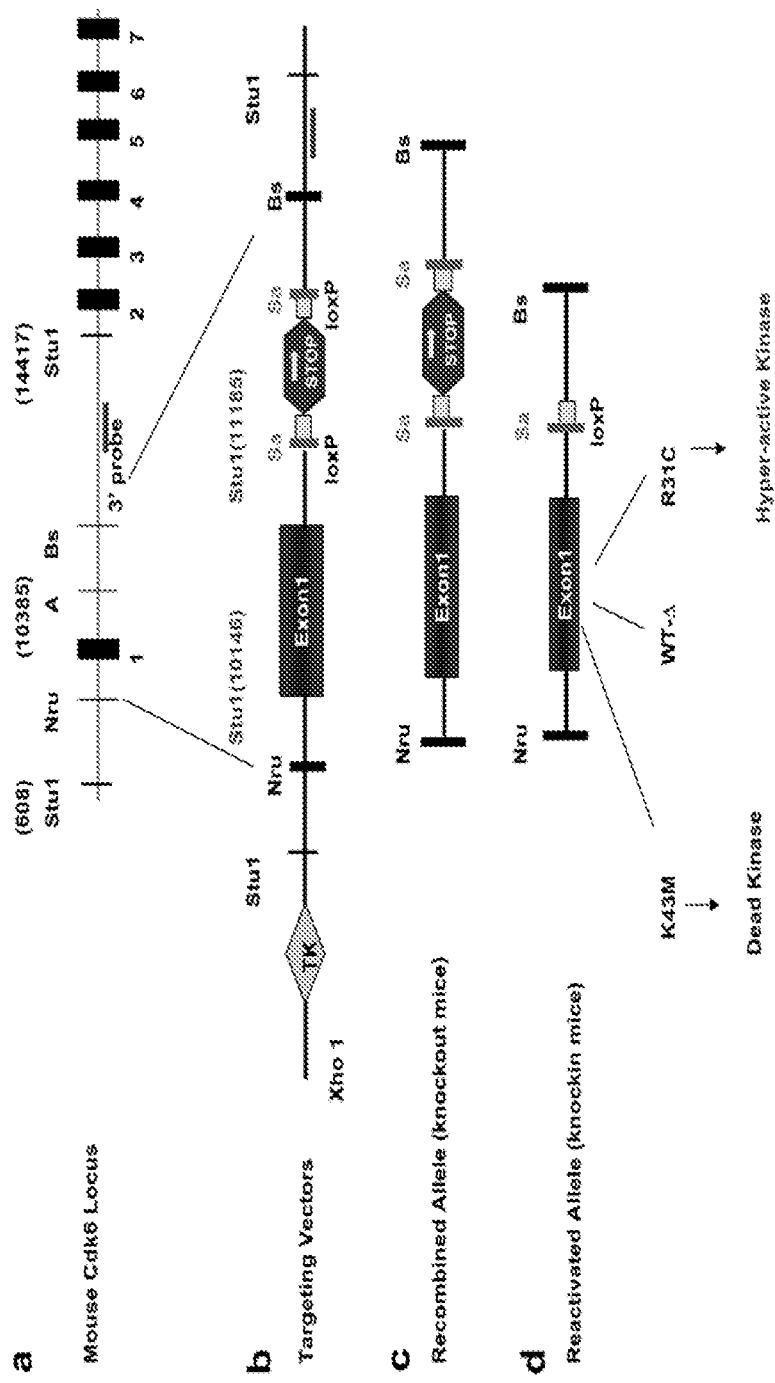
FIG. 1 shows gene targeting of mouse Cdk6 locus. Targeting strategy (a) partial restriction map of the Cdk6 gene in WT 129Sv/J mice. 7 exons are shown in boxes and numbered. (b) the targeting vector. (c) Schematic diagram of the predicted targeted Cdk6 recombined alleles after homologous recombination. (d) Schematic diagram of the predicted WT and mutant alleles (reactivated alleles) after Cre recombinase.

To facilitate an understanding of the present disclosure, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having a metabolic disease" refers to a subject that presents one or more symptoms indicative of a metabolic disease. A subject suspected of having a metabolic disease may also have one or more risk factors. A subject suspected of having metabolic disease has generally not been tested for metabolic disease. However, a "subject suspected of having metabolic disease" encompasses an individual who has received a preliminary diagnosis but for whom a confirmatory test has not been done or for whom the level or severity of metabolic disease is not known.

As used herein, the term "subject diagnosed with a metabolic disease" refers to a subject who has been tested and found to have a metabolic disease. As used herein, the term "initial diagnosis" refers to a test result of initial metabolic disease that reveals the presence or absence of disease.

As used herein, the term "subject at risk for metabolic disease" refers to a subject with one or more risk factors for developing a specific metabolic disease. Risk factors include, but are not limited to, gender, age, genetic predisposition, environmental exposure, and previous incidents of metabolic disease, preexisting non-fibrotic diseases, and lifestyle.

As used herein, the term "non-human animals" refers to all non-human animals including, but not limited to, vertebrates such as rodents, non-human primates, ovines, bovines, ruminants, lagomorphs, porcines, caprines, equines, canines, felines, aves, etc.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., fibrosis or cancer). Test compounds comprise both known and potential therapeutic compounds. A test compound can be determined to be therapeutic by screening using the screening methods of the present disclosure.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present disclosure.

As used herein, the term "effective amount" refers to the amount of a compound (e.g., a compound described herein) sufficient to effect beneficial or desired results. An effective amount can be administered in one or more administrations, applications or dosages and is not limited to or intended to be limited to a particular formulation or administration route.

As used herein, the term "co-administration" refers to the administration of at least two agent(s) (e.g., CDK6 inhibitor compound having a structure presented above or elsewhere described herein) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, or ex vivo.

As used herein, the term "toxic" refers to any detrimental or harmful effects on a cell or tissue as compared to the same cell or tissue prior to the administration of the toxicant.

DETAILED DESCRIPTION OF THE DISCLOSURE

Provided herein are compositions and method for treating or preventing metabolic disorders. In particular, provided herein are compositions, methods, and uses of CDK6 inhibitors for treating and preventing metabolic diseases (e.g., diabetes, obesity, and cardiovascular disease).

In mammals including humans, fat is stored in white adipose tissue (WAT) in the form of triglyceride, whereas brown fat cells expressing the uncoupling protein 1 (UCP-1) have the ability to burn energy through adaptive thermogenesis (Lowell B B, Spiegelman B M. Nature 2000; 404:652-60; Rosen E D, Walkey C J, Puigserver P, Spiegelman B M. Genes Dev 2000; 14:1293-307). On the other hand, inducible-brown adipocytes (beige or brite cells) are found sporadically in WAT of adult rodents and human with similar features as classical brown adipocytes (Cypess A M, Lehman S, Williams G, et al. N Engl J Med 2009; 360: 1509-17; van Marken Lichtenbelt W D, Vanhommerig J W, Smulders N M, et al. N Engl J Med 2009; 360:1500-8).

The appearance of beige cells is associated with a protection against obesity and metabolic diseases in rodent models (Seale P, Conroe H M, Estall J, et al. J Clin Invest 2011; 121:96-105; Cederberg A, Gronning L M, Ahren B, Tasken K, Carlsson P, Enerback S. Cell 2001; 106:563-73). However, little is known about the regulatory circuits controlling white fat browning. A number of coactivators have been involved in the conversion, with PPARγ co-activator 1α (PGC-1α) being a prime candidate regulator (Picard F, Gehin M, Annicotte J, et al. Cell 2002; 111:931-41; Puigserver P, Wu Z, Park C W, Graves R, Wright M, Spiegelman B M. Cell 1998; 92:829-39). Thus, identifying the mechanisms underlying beige adipocyte biogenesis is important to develop new therapeutics for obesity, diabetes and other metabolic diseases.

Cyclin-dependent Kinase 6 (CDK6) acts as an important cell cycle regulator of the G1-S phase transition (Sherr C J, Roberts J M. Genes Dev 1995; 9:1149-63) by negatively phophorylating the retinoblastoma protein (pRB). It also plays an important role in a non-cell cycle dependent manner, for example by binding and promoting the degradation of EYA2 (Kohrt D, Crary J, Zimmer M, et al. Cell Cycle 2014; 13:62-71) and RUNX1 (Biggs J R, Peterson L F, Zhang Y, Kraft A S, Zhang D E. Mol Cell Biol 2006; 26:7420-9) thereby affecting development and tumorigenesis.

Ablation of the CDK6 upstream activator Notch or AKT in mice promotes browning of white adipose tissue (Bi P, Shan T, Liu W, et al. Nat Med 2014; 20:911-8) and ameliorates diet-induced obesity (DIO) and associated insulin resistance (IR) (Bi P, Shan T, Liu W, et al. Nat Med 2014; 20:911-8; Wan M, Easton R M, Gleason C E, et al. Mol Cell Biol 2012; 32:96-106). Furthermore, it was recently found that mice deficient for CDK6 have reduced hematopoietic stem cells (LSK) which are able to give rise to adipocytes (Sera Y, LaRue A C, Moussa O, et al. Exp Hematol 2009; 37:1108-20, 20 el-4). CDK6 deficient mice also have decreased T cells (Hu M G, Deshpande A, Enos M, et al. Cancer Res 2009; 69:810-8; Hu M G, Deshpande A, Schlichting N, et al. Blood 2011; 117:6120-31), which play an important role in the initiation and perpetuation of adipose tissue inflammation as well as the development of IR (Kintscher U, Hartge M, Hess K, et al. Arterioscler Thromb Vasc Biol 2008; 28:1304-10; Rausch M E, Weisberg S, Vardhana P, Tortoriello D V. Int J Obes (Lond) 2008; 32:451-63; Wu H, Ghosh S, Perrard X D, et al. Circulation 2007; 115:1029-38), the first step in the development of Type 2 diabetes (Saltiel A R. Cell 2001; 104:517-29).

Experiments conducting during the course of development of embodiments of the present disclosure identified CDK6 as an important regulator of white fat browning (See. e.g., Examples 1 and 2). Accordingly, provided herein are methods and uses for treating and preventing metabolic disorders by inhibiting CDK6 activity.

I. CDK4/6 Inhibitors

The present disclosure is not limited to particular CDK4/6 inhibitors. The terms "CDK6 inhibitor" and "CDK4/6" inhibitor are used interchangeably to refer to inhibitors of CDK6 and/or CDK4. Examples include, but are not limited to, a nucleic acid, a small molecule, peptide, or an antibody.

In some embodiments, the CDK4/6 inhibitor is a small molecule (e.g., PD0332991; See e.g., U.S. Pat. No. 9,259, 399; herein incorporated by reference in its entirety; or LEEO11 (Ribociclib; Novartis, Basel, Switzerland; and LY2835219 (Abemaciclib; Eli Lilly and Co., Indianapolis, Ind.)).

PD0332991 (palbociclib) has the structure:

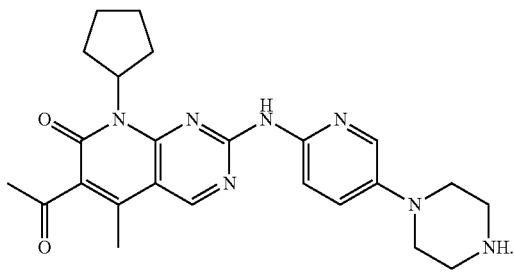 [SMILES: CC(=O)c1c(C)c2cnc(Nc3ccc(N4CCNCC4)cn3)nc2n(C2CCCC2)c1=O]

Palbociclib has been approved for the treatment of estrogen positive breast cancer in combination with letrozole and is commercially available from Pfizer (Mission, Kans.).

Ribociclib has the structure:

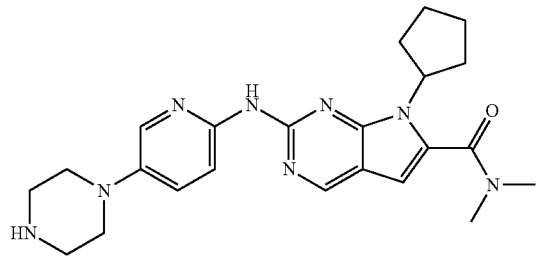 [SMILES: CN(C)C(=O)c1cc2cnc(Nc3ccc(N4CCNCC4)cn3)nc2n1C1CCCC1]

and is in clinical studies for the treatment of epithelioid sarcoma.

Abemacicilib has the structure

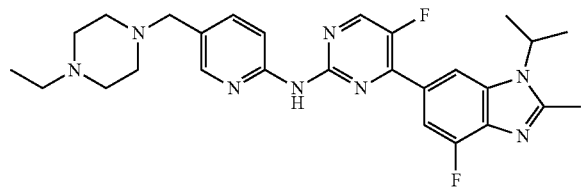 [SMILES: CCN1CCN(Cc2ccc(Nc3ncc(F)c(-c4cc(F)c5nc(C)n(C(C)C)c5c4)n3)nc2)CC1]

and is in clinical studies for the treatment of breast cancer. Additional small molecule CDK4/6 inhibitors include, but are not limited to, Flavopiridol (Alvocidib; Tolero Pharmaceuticals, Lehi, Utah), AT7519 (Astex Pharmaceuticals, Pleasanton, Calif.), JNJ-7706621 (Selleckchem, Houston, Tex.), and P276-00 (Selleckchem, Houston, Tex.). In some embodiments, the CDK4/6 inhibitor is selected from those described in the publications listed in: US20070027147; US20030229026; US 20040048915; US20040006074; US20070179118; WO2016040848; WO2016015597; WO2016014904; WO2015/180642; WO2015101293;

US20140350244; WO2014183520; WO2011101409; WO2011101417; US20130184285; US 20100160340, each of which is incorporated by reference herein in its entirety.

In some embodiments, the CDK6 inhibitor is a nucleic acid. Exemplary nucleic acids suitable for inhibiting CDK6 (e.g., by preventing expression of CDK6) include, but are not limited to, antisense nucleic acids, miRNAs, and shRNAs. In some embodiments, nucleic acid therapies are complementary to and hybridize to at least a portion (e.g., at least 5, 8, 10, 11, 12, 13, 14, 15, 16, 17, 18, 19, or 20 nucleotides) of SEQ ID NO:1 (CDK6 mRNA; accession No. NM_001259). In some embodiments, the nucleic acid hybridizes to or is complementary to at least a portion of nucleotides 413 to 1393 of SEQ ID NO:1.

In some embodiments, compositions comprising oligomeric antisense compounds, particularly oligonucleotides are used to modulate the function of nucleic acid molecules encoding CDK6, ultimately modulating the amount of CDK6 expressed. This is accomplished by providing antisense compounds that specifically hybridize with one or more nucleic acids encoding CDK6. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of CDK6. In the context of the present disclosure, "modulation" means either an increase (stimulation) or a decrease (inhibition) in the expression of a gene. For example, expression may be inhibited to treat or prevent a metabolic disorder.

In some embodiments, nucleic acids are siRNAs. "RNA interference (RNAi)" is the process of sequence-specific, post-transcriptional gene silencing initiated by a small interfering RNA (siRNA). During RNAi, siRNA induces degradation of target mRNA with consequent sequence-specific inhibition of gene expression.

An "RNA interference," "RNAi," "small interfering RNA" or "short interfering RNA" or "siRNA" or "short hairpin RNA" or "shRNA" molecule, or "miRNA" is a RNA duplex of nucleotides that is targeted to a nucleic acid sequence of interest, for example, SIN3A. As used herein, the term "siRNA" is a generic term that encompasses all possible RNAi triggers. An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In certain embodiments, the siRNAs are targeted to the sequence encoding SIN3A. In some embodiments, the length of the duplex of siRNAs is less than 30 base pairs. In some embodiments, the duplex can be 32, 31, 30, 29, 28, 27, 26, 25, 24, 23, 22, 21, 20, 19, 18, 17, 16, 15, 14, 13, 12, 11 or 10 base pairs in length. In some embodiments, the length of the duplex is 19 to 32 base pairs in length. In certain embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24, 25, 26 or 27 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

As used herein, Dicer-substrate RNAs (DsiRNAs) are chemically synthesized asymmetric 25-mer/27-mer duplex RNAs that have increased potency in RNA interference compared to traditional siRNAs. Traditional 21-mer siRNAs are designed to mimic Dicer products and therefore bypass interaction with the enzyme Dicer. Dicer has been recently shown to be a component of RISC and involved with entry of the siRNA duplex into RISC. Dicer-substrate siRNAs are designed to be optimally processed by Dicer and show increased potency by engaging this natural processing pathway. Using this approach, sustained knockdown has been regularly achieved using sub-nanomolar concentrations. (U.S. Pat. No. 8,084,599; Kim et al., Nature Biotechnology 23:222 2005; Rose et al., Nucleic Acids Res., 33:4140 2005).

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional siRNAs. "miRNAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional miRNAs or siRNAs. "Artificial miRNA" or an "artificial miRNA shuttle vector", as used herein interchangeably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (.about.35 nucleotides upstream and .about.40 nucleotides downstream) arise from restriction enzyme sites within the multiple cloning site of the siRNA. As used herein the term "miRNA" encompasses both the naturally occurring miRNA sequences as well as artificially generated miRNA shuttle vectors.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal or a sequence of six Ts.

The present disclosure contemplates the use of any genetic manipulation for use in modulating the expression of CDK6. Examples of genetic manipulation include, but are not limited to, gene knockout (e.g., removing the CDK6 gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present disclosure, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably 108 to 1011 vector particles added to the perfusate.

In some embodiments, the present disclosure provides antibodies that inhibit CDK6. Any suitable antibody (e.g., monoclonal, polyclonal, or synthetic) may be utilized in the therapeutic methods disclosed herein. In some embodiments, the antibodies are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, candidate CDK6 inhibitors are screened for activity (e.g., using the methods described in Examples 1 and 2 below or another suitable assay).

The present disclosure further provides pharmaceutical compositions (e.g., comprising the compounds described above). The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present disclosure may be formulated into any of many possible dosage forms such as, but not limited to, tablets, capsules, liquid syrups, soft gels, suppositories, and enemas. The compositions of the present disclosure may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present disclosure the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present disclosure. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present disclosure may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on EC50s found to be effective in in vitro and in vivo animal models or based on the examples described herein. In general, dosage is from 0.01 µg to 100 g per kg of body weight, and may be given once or more daily, weekly, monthly or yearly. In some embodiments, PD0332991 is administered at a dose of 10-200 mg daily and LEEO11 is administered at a dose of 100-1000 mg daily), although other dosages are specifically contemplated. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

II. Methods of Treating and Preventing Metabolic Disorders

Provided herein are methods of treating and preventing metabolic disorders through the inhibition of CDK4/6. The present disclosure is not limited to particular metabolic diseases or disorders. Examples include, but are not limited to, type II diabetes, obesity, metabolic syndrome, cardiovascular disease, elevated blood pressure, elevated fasting plasma glucose, or high serum triglycerides.

In some embodiments, CDK6 inhibitors convert white fat to brown fat in the subject. In some embodiments, the subject is or is not overweight or obese. In some embodiments, the subject exhibits or does not exhibit symptoms of the metabolic disease. For example, in some embodiments, CDK6 inhibitors are administered to a subject found to be at risk for a metabolic disorder (e.g., a subject exhibiting one or more markers or symptoms of a metabolic syndrome but not meeting the diagnostic criteria for diagnosis of a metabolic disorder).

In some embodiments, the compounds and pharmaceutical compositions described herein are administered in combination with one or more additional agents, treatment, or interventions (e.g., agents, treatments, or interventions useful in the treatment of metabolic disorders). Examples include, but are not limited to, metformin, sulfonylureas, thiazolidinediones, dipeptidyl peptidase-4 inhibitors, SGLT2 inhibitors, glucagon-like peptide-1 analog, thiazolidinediones, angiotensin-converting enzyme inhibitors (ACEIs), insulin, and weight loss surgery.

EXPERIMENTAL

The following examples are provided in order to demonstrate and further illustrate certain preferred embodiments and aspects of the present disclosure and are not to be construed as limiting the scope thereof.

Example 1

By using Cdk6 mutant mice, it was found that mice without CDK6 protein (Cdk6$^{-/-}$) or its kinase activity (K43M) display significantly increased beige cell formation, enhanced energy expenditure, better glucose tolerance and improved insulin sensitivity, and are more resistant to high fat diet-induced obesity. Re-expression of CDK6 in mature fat cells of Cdk6$^{-/-}$ mice or ablation of Runx1 in mature fat cells of K43M mice reverses white fat browning, enhanced energy expenditure, and beneficial metabolic effects observed in Cdk6$^{-/-}$ or K43M mice. The findings reveal an unprecedented function of CDK6 kinase activity in negatively regulating the conversion of fat-storing cells into fat-burning cells by suppressing RUNX1, and as such provide a target for therapeutic intervention of obesity and related metabolic diseases.

FIG. 1 shows generation of CDK6 knockout and knockin mice (Hu M G, Deshpande A, Enos M, et al. Cancer Res 2009; 69:810-8; Hu M G, Deshpande A, Schlichting N, et al. Blood 2011; 117:6120-31). Genetically distinct animals (FIG. 1) were generated by introducing a LoxP flanked transcriptional STOP cassette (LSL cassette) into intron 1 of the Cdk6 gene adjacent to the intact/mutant exon 1 (Hu M G, Deshpande A, Enos M, et al. Cancer Res 2009; 69:810-8; Hu M G, Deshpande A, Schlichting N, et al. Blood 2011; 117:6120-31). The knock-in mutants include R31C, a hyperactive, inhibitor-resistant kinase that cannot interact with INK4 family inhibitor proteins (Pavletich N P. J Mol Biol 1999; 287:821-8), and a catalytically inactive kinase (K43M) (Hu M G, Deshpande A, Schlichting N, et al. Blood 2011; 117:6120-31). The R31C mutant mimics hyperactivation of CDK6 in the cells, whereas the catalytic inactive K43M models pharmacological inhibition of kinase activity. Thus, these mouse models (all the mice have been backcrossed with C57BL/6J background for more than 9 generations) in hand are suitable to assess the relative contribution of CDK6 kinase activity and non-catalytic activity to development and cancer.

In the absence of CRE, WT/mutant K43M/R31C CDK6 protein expression is prevented, resulting in a null allele (Cdk6−/− or KO) (FIG. 1c). Upon excision of the cassette by CRE (FIG. 1d), the Cre-reactivated wild-type allele or the mutant alleles express WT or mutant K43M/R31C CDK6, respectively, from the endogenous locus with intact regulatory controls.

Figure 2:
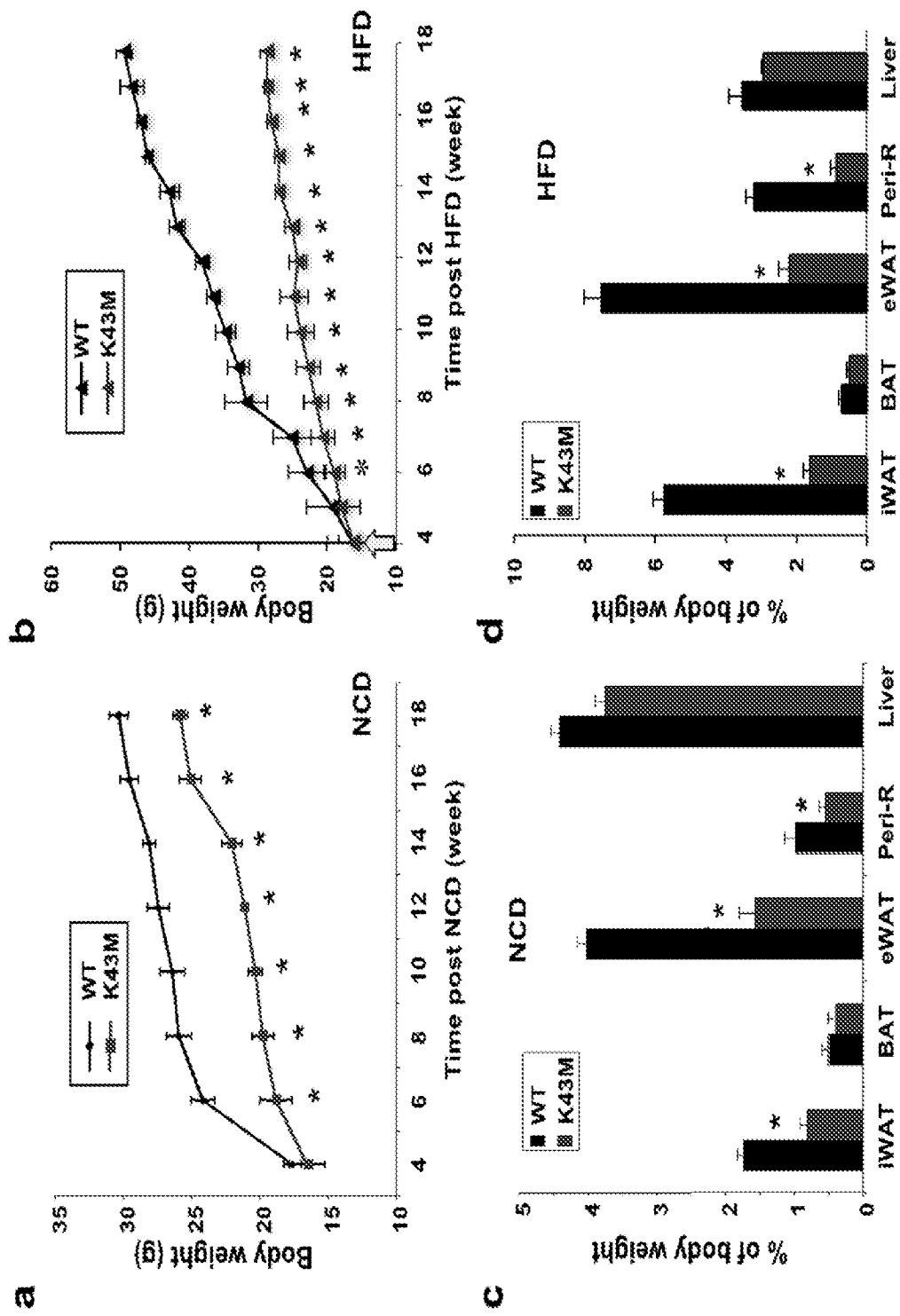
FIG. 2 shows loss of kinase activity in mice led to resistance to HFD-induced obesity, less fat pad mass, better glucose tolerance, and improved insulin sensitivity. (a,b) Body weight of age-matched male mice on NCD (a) or HFD (b) for 14-week observation time. HFD started at age of 4 weeks. (c,d) Mass of various fat pads was normalized to body weight of male mice on NCD (c) or HFD (d) at age of 18 weeks. (e,f) GTT after 18 weeks on NCD (e) or HFD (f). (g,h) ITT after 18 weeks on NCD (g) or HFD (h). For a-h, data shown are mean±S.E. (n=10 for each group), *p<0.05, t-test, vs WT.
Figure 2:
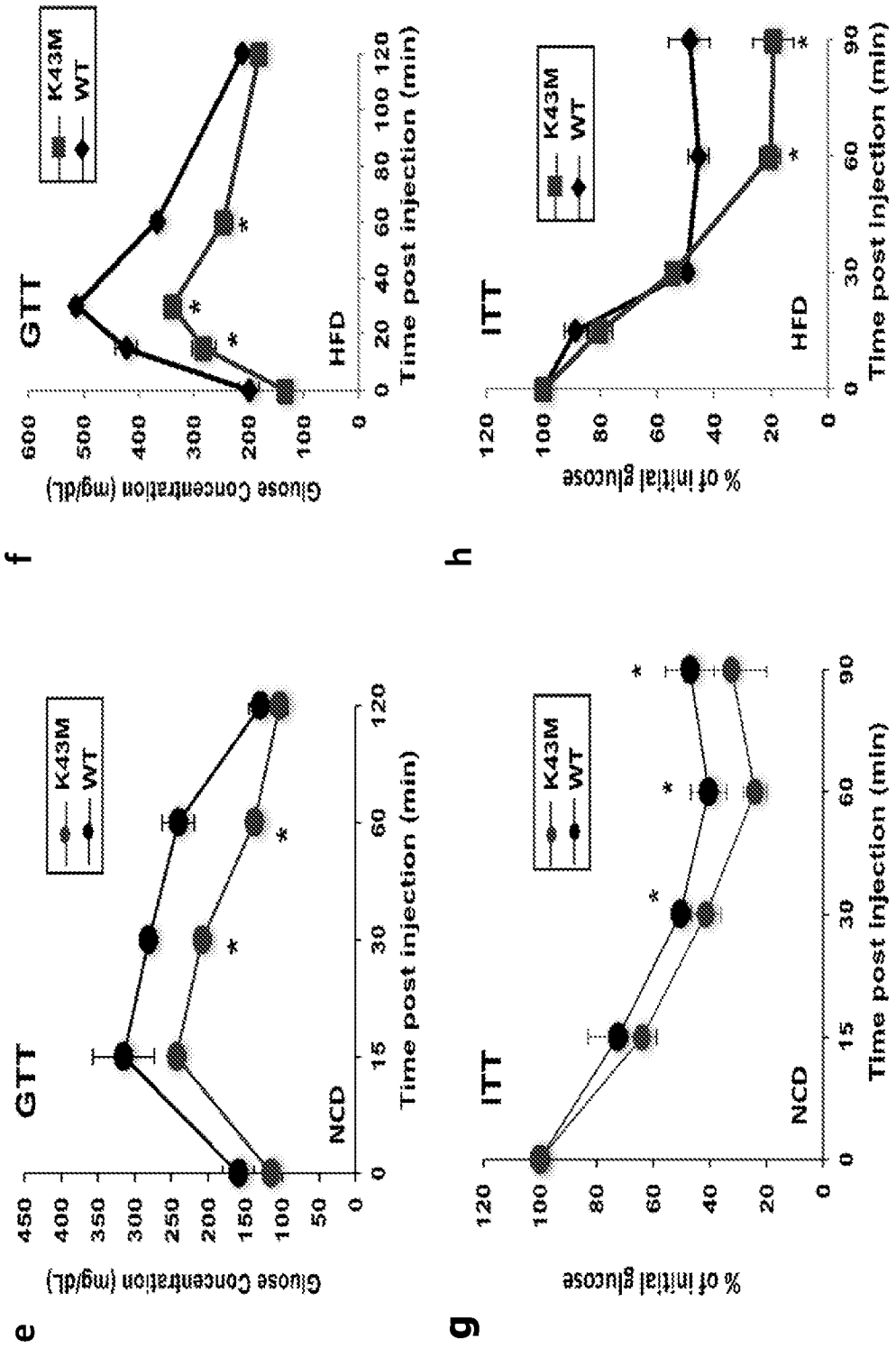

FIG. 2 shows that K43M mice are leaner under NCD with reduced fat pad mass, improved glucose metabolism, and more resistant to high fat diet-induced obesity. Both male (FIG. 2) and female K43M mice were found to be lean under NCD (FIG. 2a). To investigate the role of CDK6 kinase activity in HFD induced obesity, mice were challenged with a HFD for 14 weeks starting at 4 weeks of age (FIG. 2b). Notably, at ~18 weeks of age, under both NCD and HFD (FIG. 2c,d), K43M mice had significantly decreased fat pad mass (~1.5- to 4-fold reduction) in all WAT depots analyzed, including iWAT, eWAT, and perirenal (Peri-R) compartments, which far exceeds the marginal decrease in the body weight compared to WT mice (~16% reduction under NCD, 47% reduction under HFD). The size of WAT in K43M mice is not due to hypophagia as K43M mice had significantly more food intake (0.210±0.012 g/g of BW/day) than WT mice (0.134±0.006 g/g of BW/day). By contrast, interscapular BAT depots were not significantly different in weight between WT and K43M mice (FIG. 2c,d). In addition, no significant changes were observed in the masses of livers between WT and K43M mice under NCD and HFD (FIG. 2c,d).

It was next evaluated whether K43M mice had beneficial metabolic effects by conducting intraperitoneal glucose- and insulin-tolerance tests (IP-GTT and IP-ITT, respectively). Compared to their WT littermates, K43M mice fed on both NCD and HFD displayed rapid clearance and resulted in lower blood glucose concentrations after glucose (FIG. 2e,f)

and insulin (FIG. 2g,h) injection, showing that genetic disruption of CDK6 improves blood glucose tolerance and insulin sensitivity.

Figure 3:
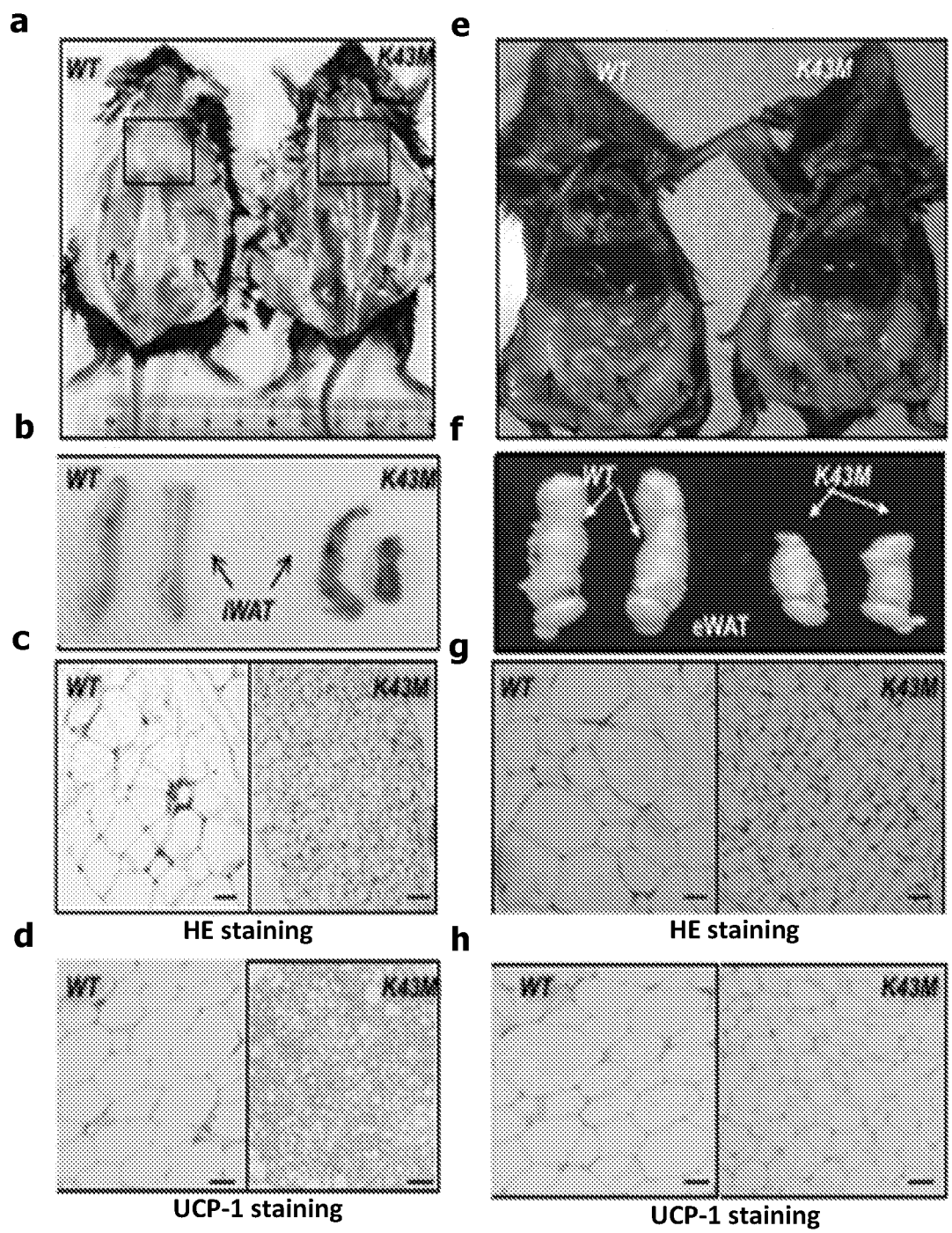
FIG. 3 shows that loss of CDK6 kinase activity in mice induced white fat browning. (a,e) Appearance of male posterior-subcutaneous WAT (sWAT) (a), and dorsal view of NCD fed WT and K43M mice (e), emphasized with blue squares and arrows. (b,f) Appearance of a close view of the iWAT (b) and eWAT (f) from the mice indicated. (c,g) Representative light microscopic images of H&E-stained sections of iWAT (n=6) and eWAT (n-6) from male mice indicated (scale bars: 100 µm). (d,h) Representative images of UCP-1 staining (n=6) of iWAT and eWAT from mice indicated at 18 weeks of age (scale bars: 100 µm). (l,k) Relative mRNA expression levels of BAT-specific markers (Ucp-1, Pgc-1α, Cidea, and Prdm16) and WAT-specific markers (AP2, adiponectin-AdipoQ, and Leptin) of iWAT (i) and eWAT (k) tissues from WT and K43M mice. Data shown are fold changes of mRNA normalized to the control WT, which is arbitrarily set to 1 unit. (j) Relative expression levels of mtDNA of eWAT and iWAT from WT and K43M mice. Data shown are fold changes of mtDNA. For i and j, *p<0.05, vs WT (n=6), t-test. (1) Immunoblots of the indicated protein levels in iWAT and eWAT from 50 μg of cell lysates of different mice indicated at 18 weeks of age. α-tubulin is used as internal loading control.
Figure 3:
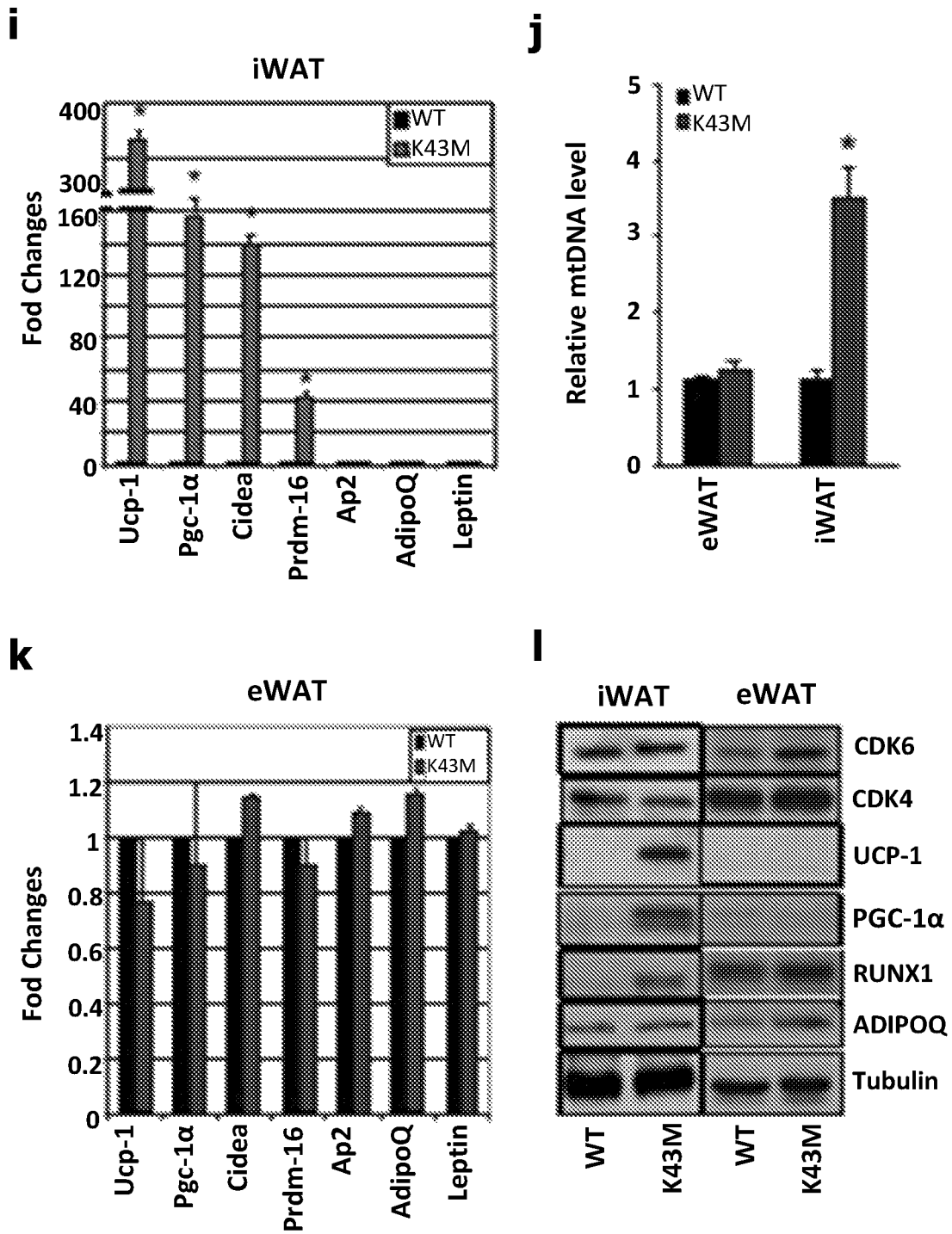

FIG. 3 shows that loss of CDK6 kinase activity in mice leads to white fat browning in subcutaneous WAT (sWAT) but not in eWAT. Under NCD, both male (FIG. 3) and female K43M mice were found on dissection to have browner appearance in various fat pads such as posterior-subcutaneous (FIG. 3a) and iWAT (FIG. 3b) than their WT counterparts. The size of adipocytes in K43M mice were smaller (FIG. 3c) but the brown-type features of iWAT were evidenced by presence of much more abundant multilocular UCP-1$^+$ beige adipocytes in iWAT (FIG. 3d). By contrast, despite reduced fat pad mass and smaller cell sizes, K43M and WT mice had similar appearance with similar UCP-1$^+$ staining in eWAT (FIG. 3e-h), showing that the underlying mechanisms governing the homeostasis of sWAT and visceral adipose tissue (VAT) of K43M mice were different. Consistently, BAT-specific genes Ucp-1, Pgc-1α, Cidea, and Prdm16 were expressed at significantly higher levels in iWAT (FIG. 3i) but not in eWAT (FIG. 3k) of K43M mice than those in WT mice. By contrast, the WAT-specific genes including Ap2, Adiponectin (AdipoQ), and Leptin were expressed at comparable levels in both iWAT and eWAT (FIG. 3i,k) from both K43M and WT mice. Furthermore, iWAT but not eWAT of K43M mice had higher expression of mitochondria DNA (mtDNA) than that of WT mice (FIG. 3j). Noticeably, UCP-1 and PGC-1, two factors contributing to leanness in various mouse models, were expressed at higher levels in iWAT of K43M mice but not eWAT than those in iWAT of WT mice (FIG. 3l), supporting the notion of greatly enhanced beige cells in the iWAT depots. Taken together, these data demonstrate that increasing white fat browning but not reduced adipogenesis of WAT may underlie the reduced fat pad mass in K43M mice under NCD.

Under the same experimental condition, it was also observed that RUNX1 protein, a downstream transcriptional target of CDK6 (Fujimoto, T., Anderson, K., Jacobsen, S. E., *Embo J* 26, 2361-2370, 2007) was increased in iWAT but not in eWAT of K43M adipocytes in comparison to their respective controls (FIG. 3l). The levels of Runx1 mRNA levels were comparable (not shown), however, ruling out a transcriptional effect of CDK6/kinase activity ablation on RUNX1 levels. Together with the known essential functions of RUNX1 in many biological programs related to development (Ichikawa, M., et al, *Nat Med* 10, 299-304, 2004), it is contemplated that RUNX1 may be involved in the process of white fat browning in iWAT of K43M mice.

Together, these data indicate that under NCD, the gross reduction of sWAT pad mass in K43M mice resulted from a partial replacement of white fat with beige cells.

Figure 4:
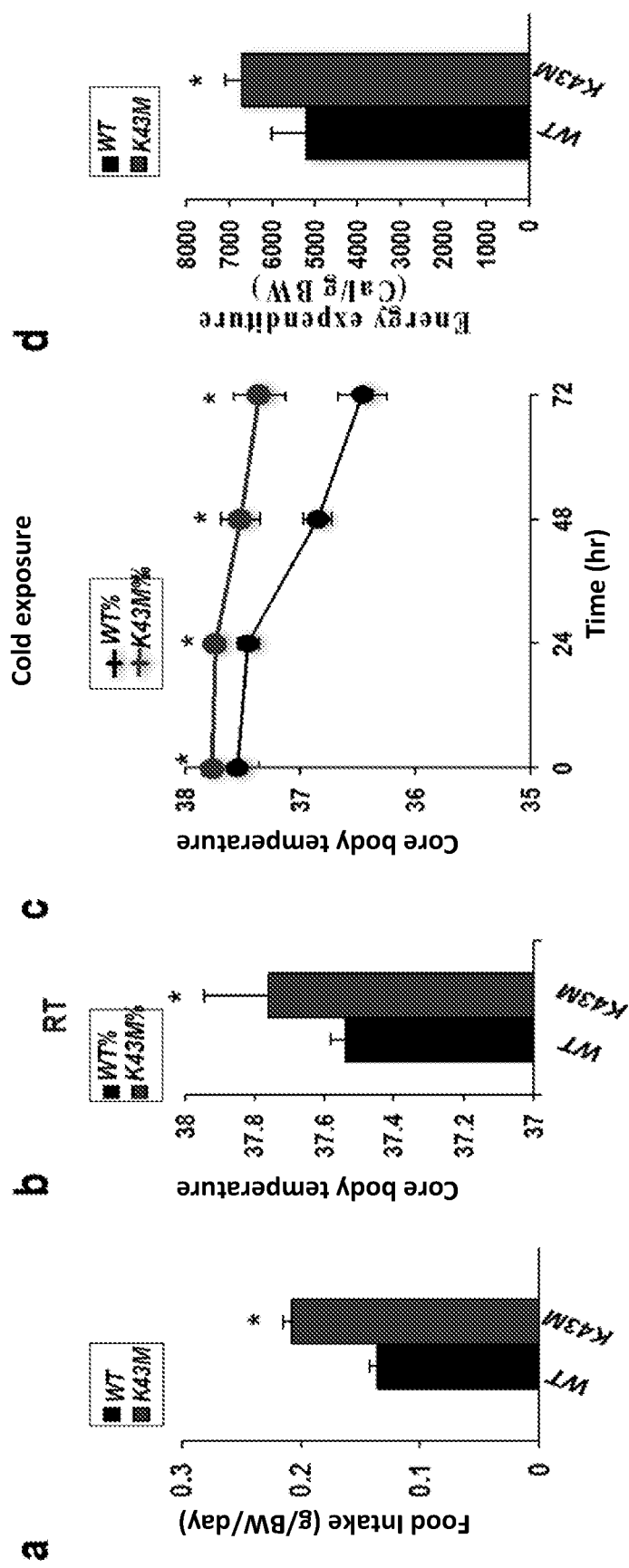
FIG. 4 shows that loss of CDK6 kinase activity in mice leads to increased food intake and body temperature, increased adaptability to cold exposure, and increased energy expenditure. (a) Bar graphs showing food intake of age-matched male WT and K43M mice. (b,c) Core body temperature of male mice at room temperature (b, RT) or at 4° C. (c) for up to 72 h (n=6 per group). (d) Energy expenditure (EE) was calculated based on the formula below: EE=(3.815+1.232×RER)×VO2/lean mass (g). For a-d, data are expressed as mean±S.E, *p<0.05, vs WT, t-test. (e,f) Oxygen consumption ($VO_2$) and $CO_2$ production ($VCO_2$) (g,h) of male WT and K43M mice on NCD (n=6) in 12 h light and dark phases. $VO_2$ and $VCO_2$ were normalized by lean mass. *p<0.05, vs WT, log-rank tests. (i) Bar graphs showing mean Respiratory Exchange Ratios (RER) over 24-hour period. RER was calculated as the volume of CO2 versus the volume of oxygen (VCO2/VO2). (j) Physical activity of male WT and K43M mice in the periods of 12 h light and 12 h dark phase. (k) Ex vivo Oxygen consumption of iWAT homogenates from different WT and K43M mice. Data are expressed as mean±S.E, *p<0.05, vs WT, t-test.
Figure 4:
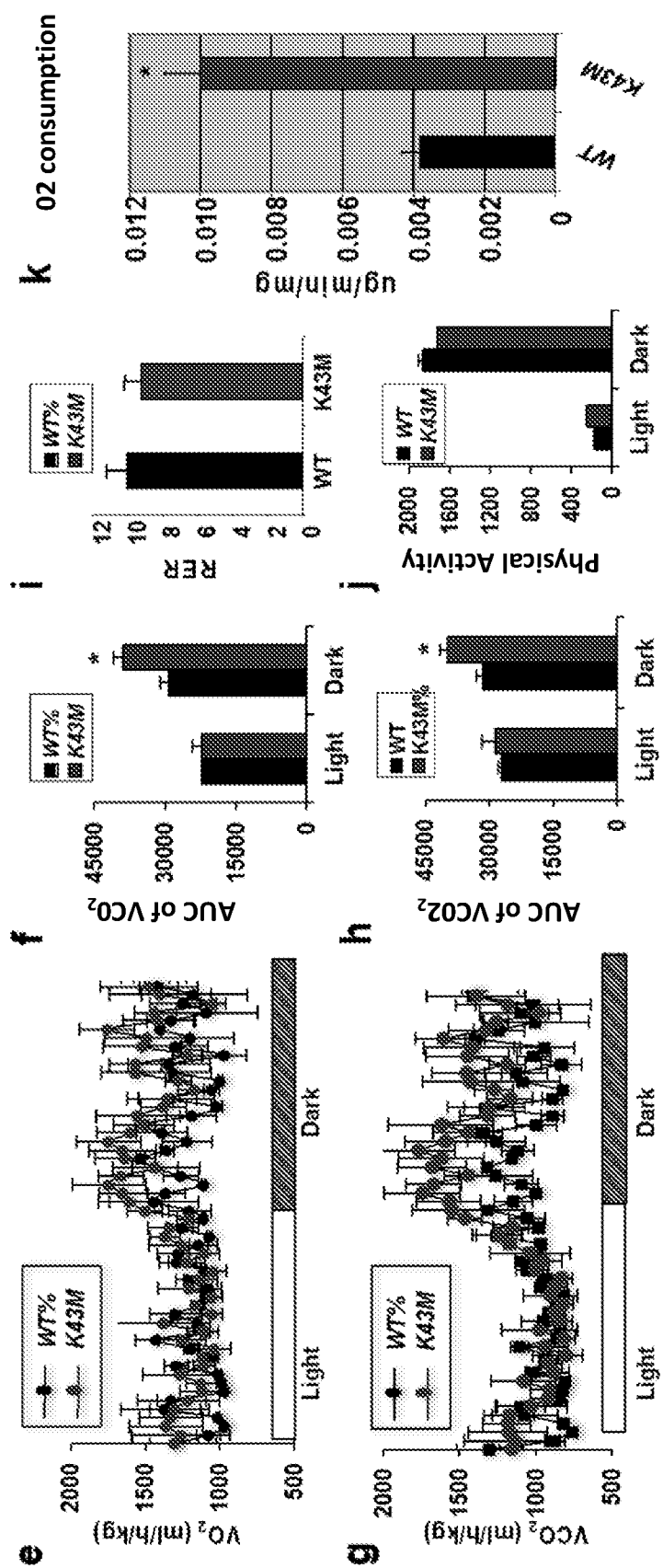

FIG. 4 shows that K43M mice display increased food intake and body temperature, increased adaptability to cold exposure, and increased energy expenditure. A physiological hallmark of beige cells is their highly active metabolism coupled to thermogenesis, similar to that featured in classical brown fat cells (Wu, J., et al. *Cell* 150, 366-376, 2012). To determine if increased browning in K43M mice correlates with increased thermogenesis, the body temperature of mice under different conditions was examined. K43M mice had increased calorie intake (FIG. 4a) and elevated body temperature compared to those of WT mice at room temperature (FIG. 4b, RT). Robust differences were apparent after cold exposure. WT mice were significantly colder than their K43M counterparts by 0.28° C. (1-day, p=0.03), 0.67° C. (2-day, p=0.02), and 0.90° C. (3-day, p=0.03), respectively (FIG. 4c). These results indicate that increased white fat browning in K43M mice is reflected by significantly higher body temperatures and thus more adaptive than WT mice to cold-induced thermogenesis.

To further investigate the mechanism underlying the difference in reduced adiposity in 18-week-old K43M mice, the metabolic activities of these mice was monitored by using metabolic cages. NCD fed K43M mice had increased energy expenditure during the three-day observation period (FIG. 4d), as indicated by significantly greater $O_2$ consumption (FIG. 4e,f, Dark phase) and greater $CO_2$ production (FIG. 4g,h, Dark phase) than WT controls during the nocturnal phase. Importantly, there is no noticeable difference in the respiration exchange ratio (RER) and physical activity between WT and K43M mice (FIG. 4i,j). These data indicated that the reduced adiposity in K43M mice might be caused by an increase in energy expenditure rather than in physical activity.

Lean mass is mainly composed of skeletal muscle, a major contributor to resting and exercising energy expenditure (Butler, A. A. & Kozak, L. P. *Diabetes* 59, 323-329, 2010). To exclude this potential confounding effect of skeletal muscle, the metabolic rate of iWAT from different WTandK43M mice was examined using a Clark electrode. When measuring the respiration rate of freshly minced fat tissue, the $O_2$ consumption of iWAT was increased significantly in K43M mice compared to that in WT mice (FIG. 4h), recapitulating the effects of loss of CDK6 kinase activity on energy expenditure in whole animals.

Collectively, these results demonstrate that loss of CDK6 kinase activity in mice results in increased thermogenic function through elevation of energy expenditure, which may account for more adaptability in response to a cold exposure and for protection against HFD-induced obesity.

Figure 5:
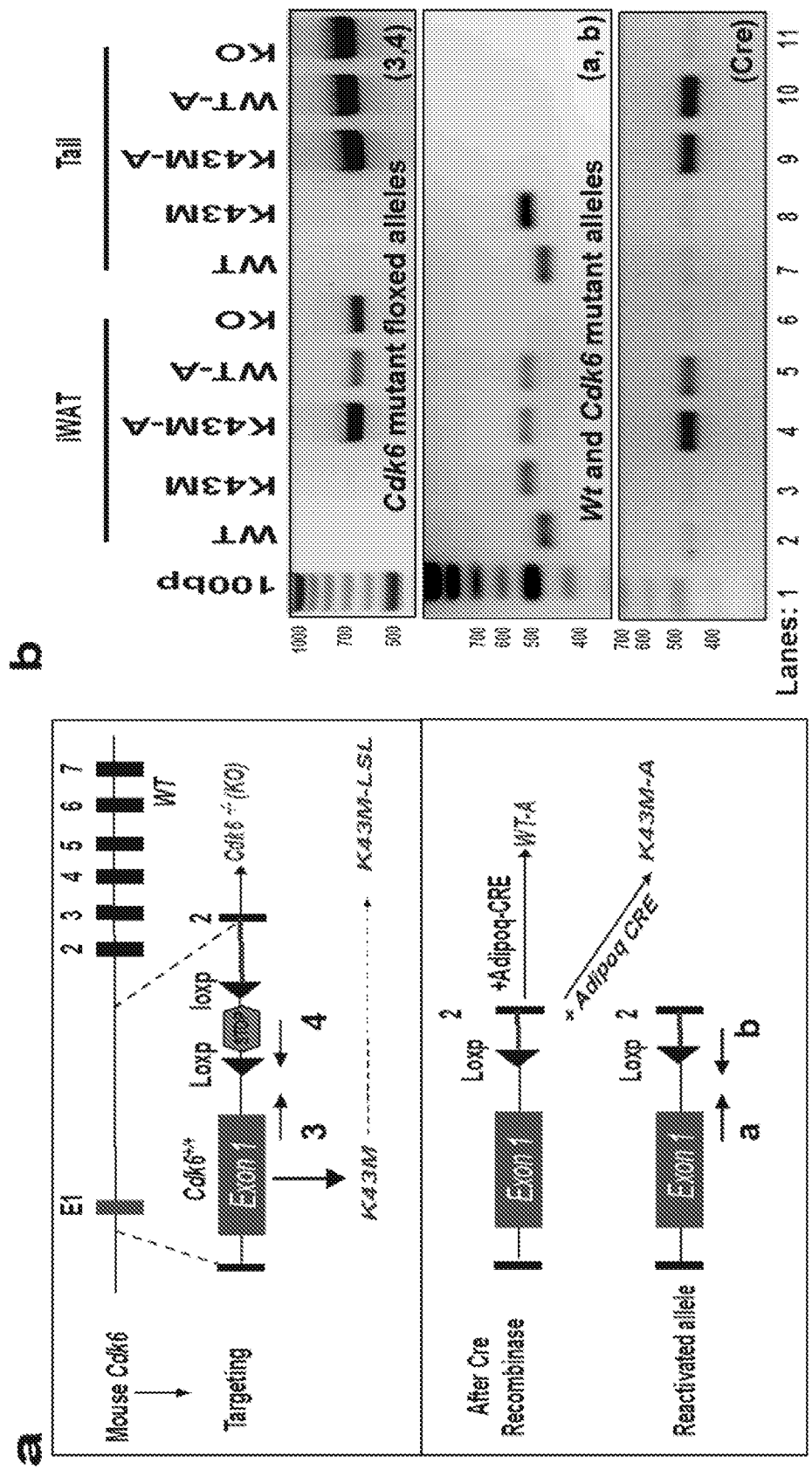
FIG. 5 shows characterization of resultant mice with adipocytes-specific expression of WT/K43M. (a) The strategy used for making Cdk6 mutant mice with adipocytes-specific expression of WT/K43M. Cdk6$^{-/-}$ mice were made as described in FIG. 1c. (b) PCR-based genotyping confirmed DNA recombination in the adipose tissues (e.g. iWAT, lanes 4 and 5) of WT-A and K43M-A mice but not in the tail DNA (lanes 9 and 10). (c and d) CDK6 protein levels of iWAT (c) and thymocytes (d) under NCD. α-Tubulin was used as an internal control. (e) Body length of different mice indicated (n=10 for each strain). (f) Food intake of different mice indicated. *p<0.05, (n=6), vs WT, t-test. ◆p<0.05, t-test, vs WT-A.
Figure 5:
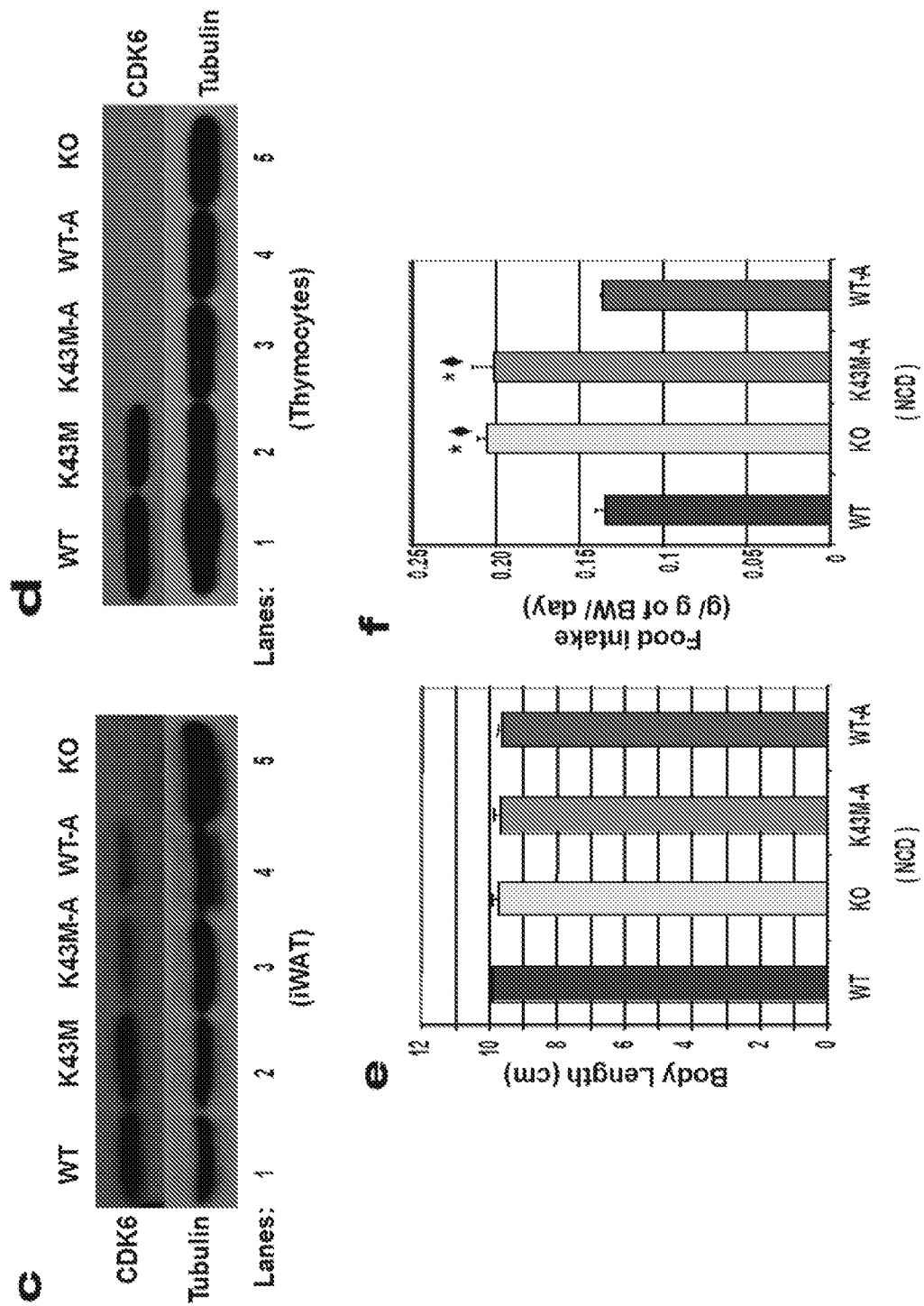

FIG. 5 shows characterization of Re-expression of CDK6 or expression of K43M in mature adipocytes of KO mice. The brown appearance of WAT in K43M mice (germline) could be a direct (cell-autonomous) consequence of loss of CDK6 kinase activity on specification and/or differentiation from beige precursors, or on a direct conversion from white adipocytes. It could also be that the effects are secondary (non-cell-autonomous) to signaling pathways that indirectly affect white fat browning, such as increased intracellular cAMP, or activation of 3-adrenergic receptors (Lafontan, M. & Berlan, M. *J Lipid Res* 34, 1057-1091, 1993).

In light of these different scenarios, the following questions were explored to delineate the mechanism responsible for beige cell activation in the setting of CDK6 loss: 1) whether re-expression of CDK6 in mature adipocytes can reverse the phenotypes observed in KO mice, and 2) whether adipose-specific expression of K43M can recapitulate the phenotypes observed in KO/K43M mice. To address these questions, Cdk6$^{-/-}$ or K43M-LSL mice were crossed with Adiponectin-Cre (Adipoq-Cre) mice (FIG. 5a, bottom panel), which express CRE in mature adipocyte (Cristancho, A. G. & Lazar, M. A. *Nat Rev Mol Cell Biol* 12, 722-734, 2011) within WAT and BAT. The resultant mice are named WT-A and K43M-A for re-expression of CDK6 or expression of K43M proteins in mature adipocytes. DNA recombination and Cre expression in adipocytes of the resultant mice were confirmed by PCR (FIG. 5b) (Hu, M. G., et al. *Blood* 117, 6120-6131, 2011). Immunoblot analysis showed that the levels of CDK6/K43M expression in WT-A and K43M-A mice were about 50-60% of WT (FIG. 5c), which shows that Adipoq-Cre elicited partially penetrant recombination in mature adipocytes and/or no observable recombination in the SVF (Lee, K. Y., et al. *Diabetes* 62, 864-874, 2013) of white adipose depots where the progenitors of beige cells reside. Consistent with this notion, NO CDK6 protein in other tissues such as thymocytes (FIG. 5d) was detected in WT-A and K43M-A mice. Consistent with previous studies (Lee, K. Y., et al. *Diabetes* 62, 864-874, 2013; Kozar, K. & Sicinski, P. *Cell Cycle* 4, 388-391, 2005), WT-A and K43M-A mice were born at the expected Mendelian frequency. They are fertile and develop normally. They have similar body lengths as WT and KO mice (FIG. 5e). Similar to K43M mice, KO and K43M-A mice are more than WT mice, whereas WT and WT-A mice had similar food intake each day (FIG. 5f).

Figure 6:
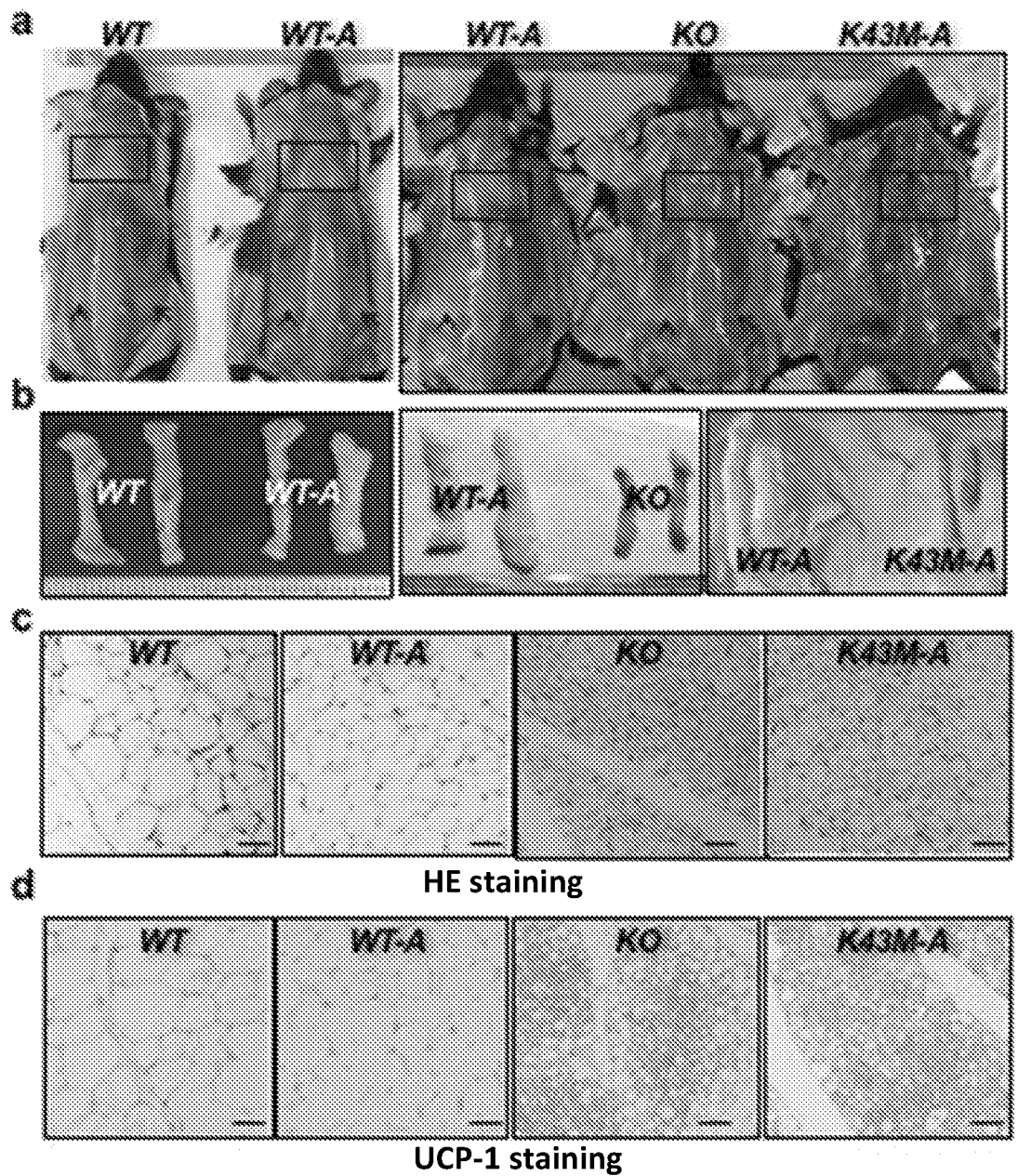
FIG. 6 shows that re-expression of CDK6 in mature adipocytes of KO mice reverses white fat browning. (a) Appearance of male posterior—sWAT of NCD—fed WT, WT-A, KO, and K43M-A, emphasized with blue squares and arrows. (b) Appearance of a close view of the iWAT from the mice indicated. (c) Representative light microscopic images of H&E-stained sections of iWAT (n=6) from male mice indicated (scale bars: 100 μm). (d) Representative images of UCP-1 staining (n=6) of iWAT from mice indicated at 18 weeks of age (scale bars: 100 μm). (e,f) Relative mRNA expression levels of BAT-specific markers (Ucp-1, Pgc-1α, Cidea, and Prdm16) of iWAT under NCD(e) and HFD (f) from mice indicated. Data shown are fold changes of mRNA normalized to their controls WT or WT-A, which is arbitrarily set to 1 unit. *p<0.05, n=6, t-test comparing vs its control. (g) Immunoblots of the indicated protein levels in iWAT and eWAT from 50 μg of cell lysates of different mice as indicated at 18 weeks of age. (h) Ex vivo Oxygen consumption of iWAT homogenates from different mice indicated. Data are expressed as mean±S.E, *p<0.05, n=6, vs WT, t-test. +p ⌐0.05, n=6 vs KO, t-test.
Figure 6:
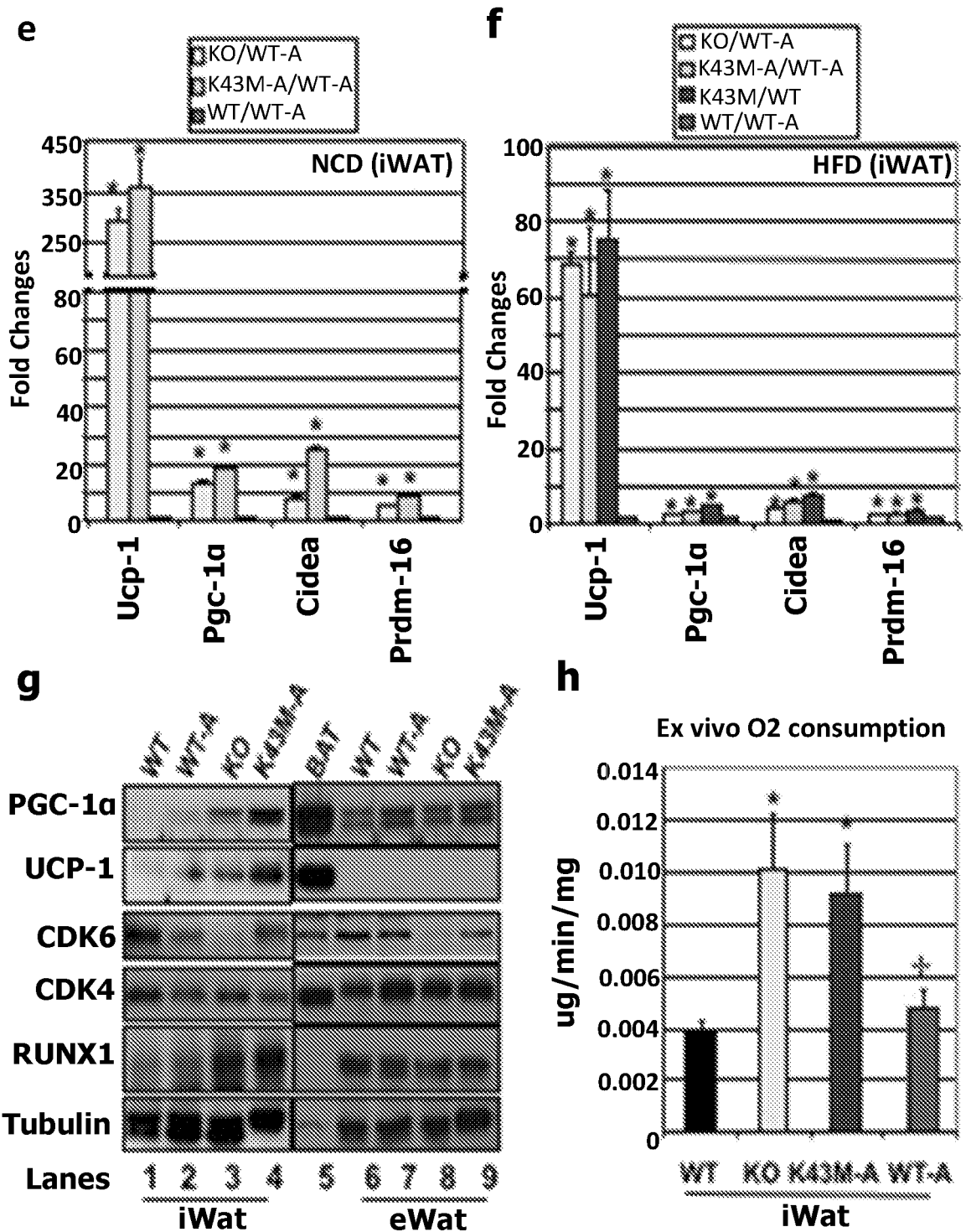

FIG. 6 shows that re-expression of CDK6 in mature adipocytes of KO mice reverses white fat browning. Loss of kinase activity in mature adipocytes preserves the effect of loss of kinase activity in germline on white fat browning. It was found that re-expression of CDK6 in mature adipose cells of WT-A mice reversed the browning of WAT, indicating that CDK6 negatively regulates white fat browning in a cell-autonomous manner, whereas expression of the inactive kinase (K43M-A) in mature adipocytes on a null background preserves the K43M or null phenotype (FIG. 6a-d). Consistently, to a similar degree as K43M versus WT, the BAT-specific genes were expressed at higher levels in iWAT of KO or K43M-A mice compared to those in their counterparts under both NCD and HFD (FIG. 6e,f). Immunoblot analysis confirmed the higher expression of UCP-1, PGC-1α, and RUNX1 (FIG. 6g) in iWAT but not in eWAT of KO and K43M-A mice. By contrast, Ap2 and AdipoQ were comparable between KO/K43M-A and WT-A mice, as in K43M iWAT (FIG. 3i) under NCD. Noticeably, all gene expression levels were comparable between WT-A and WT cells (FIG. 6e,f). Remarkably, adipose-specific re-expression of CDK6 significantly reversed the increased oxygen consumption of iWAT observed in KO mice, whereas K43M-A mice recapitulated KO mice on oxygen consumption (FIG. 6h). Taken together, these data indicate that re-expression of CDK6 in adipose tissues reversed the phenotypes observed in KO mice. Loss of kinase activity in mature adipocytes preserves the effect of loss of kinase activity in germline on white fat browning and increased energy expenditure. Thus, the evidence described here supports that CDK6 kinase activity is required for negatively regulating white fat browning in a cell-autonomous manner.

Figure 7:
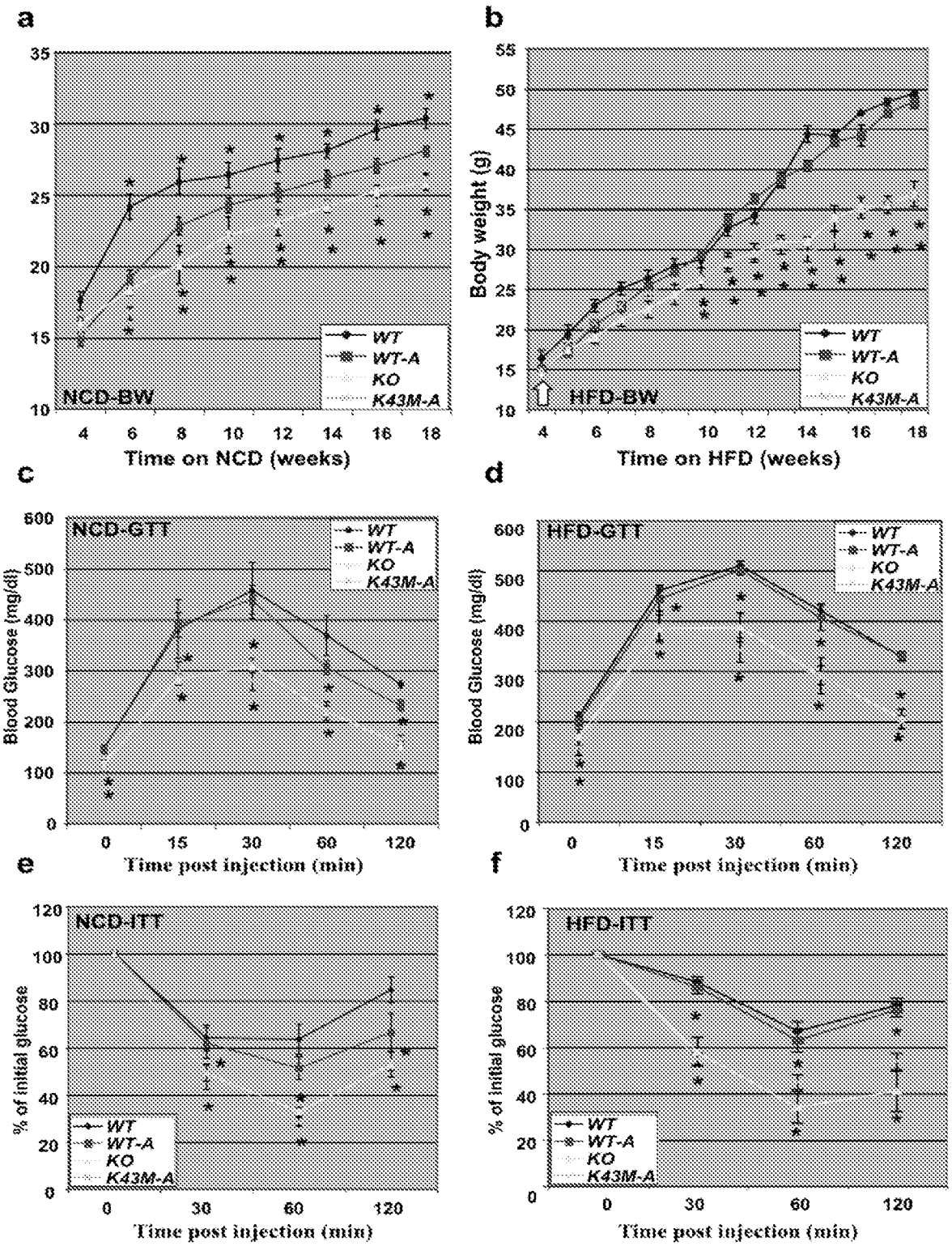
FIG. 7 shows that re-expression of CDK6 in mature adipocytes reversed the beneficial metabolic effects observed in KO mice. (a,b) Body weight of age-matched male mice on NCD (a) or HFD (b) for 14-week observation time. HFD started at age of 4 weeks. (c,d) GTT after 18 weeks on NCD (c) or HFD (d). (e,f) ITT after 18 weeks on NCD (e) or HFD (f). (g,h) Mass of various fat pads was normalized to body weight of male mice on NCD (g) or HFD (h) at age of 18 weeks.
Figure 7:
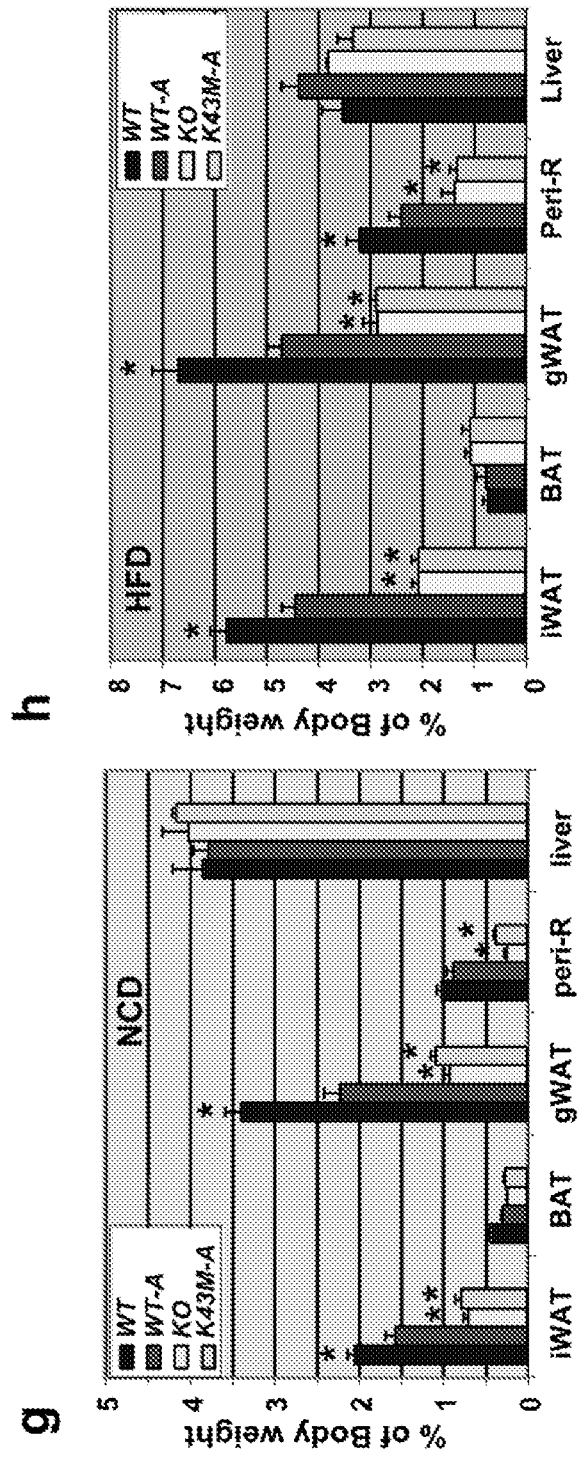

FIG. 7 shows that re-expression of CDK6 in mature adipocytes reversed the beneficial metabolic effects observed in KO mice. Loss of kinase activity in mature adipocytes recapitulates loss of kinase activity in germline with regards to the beneficial metabolic effects.

To check whether browning of WAT in K43M-A mice elicits beneficial metabolic effects like K43M mice, age-matched male K43M-A together with WT, KO, and WT-A mice were fed with a NCD or a HFD for 14 weeks starting at 4 weeks of age. KO and K43M-A mice had similar body weight under both diets, exhibiting significantly reduced body weight on both NCD (FIG. 7a) and HFD (FIG. 7b), compared to WT-A mice. Re-expression of CDK6 in mature adipocytes in WT-A mice restored the body weight completely under HFD but only partially under NCD compared to WT mice during the observation period (FIG. 7a,b), suggesting that the effects of CDK6 on the development of other tissues such as progenitors of adipocytes, thymocytes (Hu, M. G., *Cancer Res* 69, 810-818, 2009), and hematopoietic stem progenitors (Hu, M. G., et al. *Blood* 117, 6120-6131, 2011) might account for the baseline body weight difference between WT and WT-A mice fed with NCD.

Similar to K43M mice with a germline mutation, K43M-A andKO mice displayed better glucose tolerance (FIG. 7c,d), more sensitivity to insulin (FIG. 7e,f), and drastically reduced fat pad masses (FIG. 7g,h) ranging from ~2- to 3.6-fold reduction in different fat pads, compared to those of WT-A mice. Consistent with reduced weight gain observed under NCD, WT-A had slightly but significantly reduced fat pad masses in various depots compared to those of WT mice, ranging from ~1.3- to 1.6-fold reduction, suggesting re-expression of CDK6 in mature adipocytes only partially rescued the defect of KO mice in WAT development.

Together, these data indicated that adipose-specific re-expression of CDK6 partially or completely reversed beneficial metabolic effects observed in KO mice, indicating that the CDK6 kinase activity regulates metabolic homeostasis in a cell-autonomous manner. But it remains to be seen if loss of CDK6 or kinase activity ONLY in adipocytes has the beneficial effect.

Figure 8:
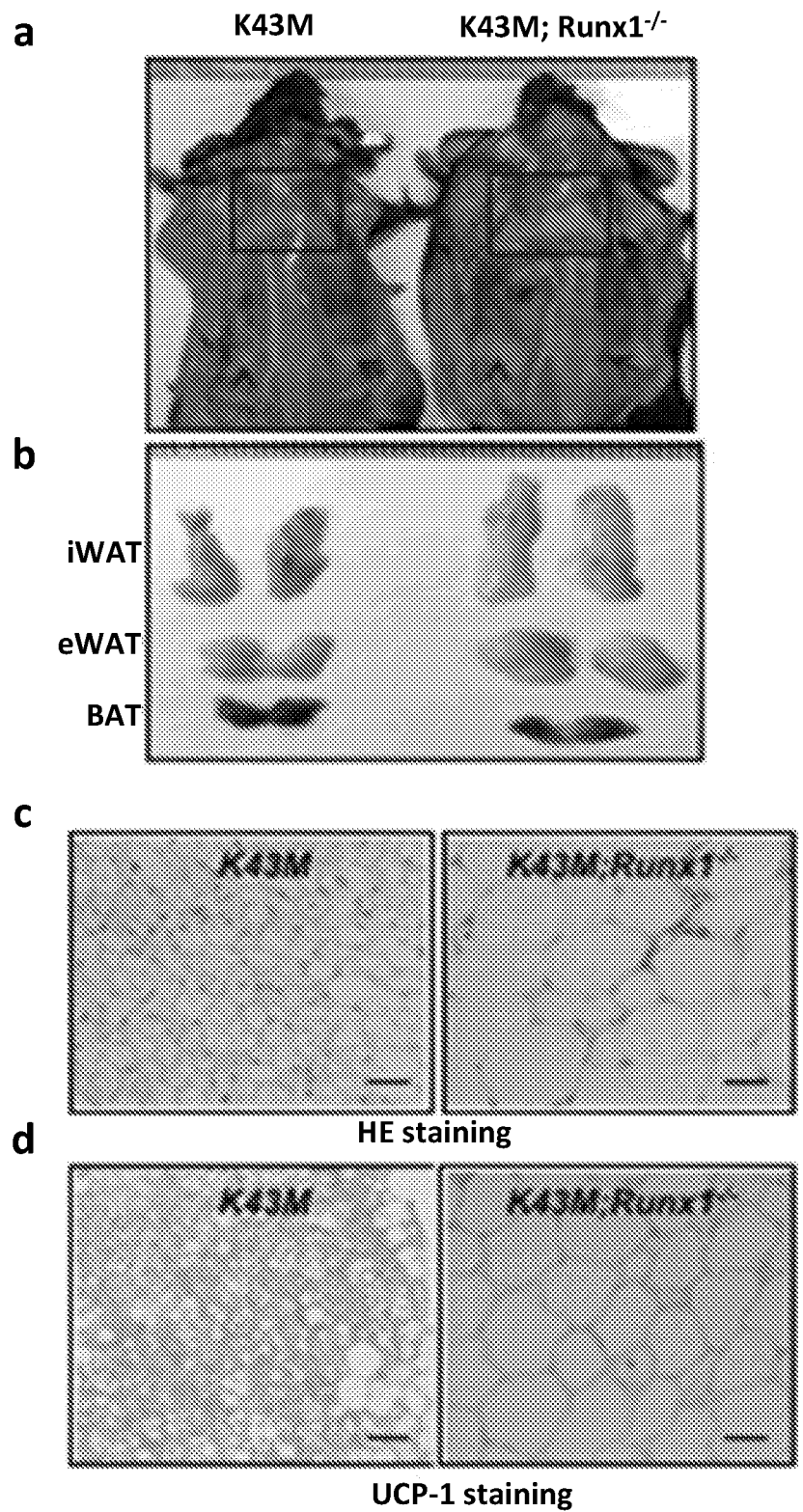
FIG. 8 shows that CDK6 inhibits white fat browning by suppressing RUNX1. (a) Appearance of male posterior-sWAT view of NCD fed K43M and K43M; Runx1$^{-/-}$, emphasized with blue squares and arrows. (b) Appearance of a close view of the iWAT (top panel), eWAT (middle panel), and BAT (bottom panel) from the mice indicated. (c) Representative light microscopic images of H&E-stained sections of iWAT (n=6) from male mice as indicated (scale bars: 100 μm). (d) Representative images of UCP-1 staining (n=6) of iWAT from mice indicated at 18 weeks of age (scale bars: 100 μm). (e) Mass of various fat pads was normalized to body weight of male mice on NCD at age of 12 weeks. Data shown are mean±S.E. (n=10 for each group), *p<0.05, t-test, vs WT. +p ⌐0.05, t-test, K43M; Runx1$^{-/-}$ vs K43M. (f) GTT after 12 weeks on NCD. (g) ITT after 12 weeks on NCD. For f and g, n=10 for each group, *p<0.05, t-test, K43M vs WT, ◆p<0.05, t-test, Runx1 vs WT, +p ⌐0.05, t-test, K43M; Runx1$^{-/-}$ vs K43M, ◆p<0.05, t-test, K43M; Runx1$^{-/-}$ vs WT. (h,i) Relative mRNA expression levels of BAT-specific markers (Ucp-1, Pgc-1α, Cidea, and Prdm16) and WAT-specific markers (AP2, Leptin, AdipoQ) of iWAT tissues from mice indicated. Data shown (h and i) are fold changes of mRNA normalized to the control WT or K43M, which is arbitrarily set to 1 unit. *p<0.05, (n=6), vs its relative control, t-test. (j) Immunoblots of the indicated protein levels in iWAT from 50 μg of cell lysates of different mice indicated at 12 weeks of age. α-tubulin is used as internal loading control. (k) Ex vivo Oxygen consumption of iWAT homogenates from mice indicated. Data are expressed as mean±S.E, *p<0.05, vs K43M, t-test.
Figure 8:
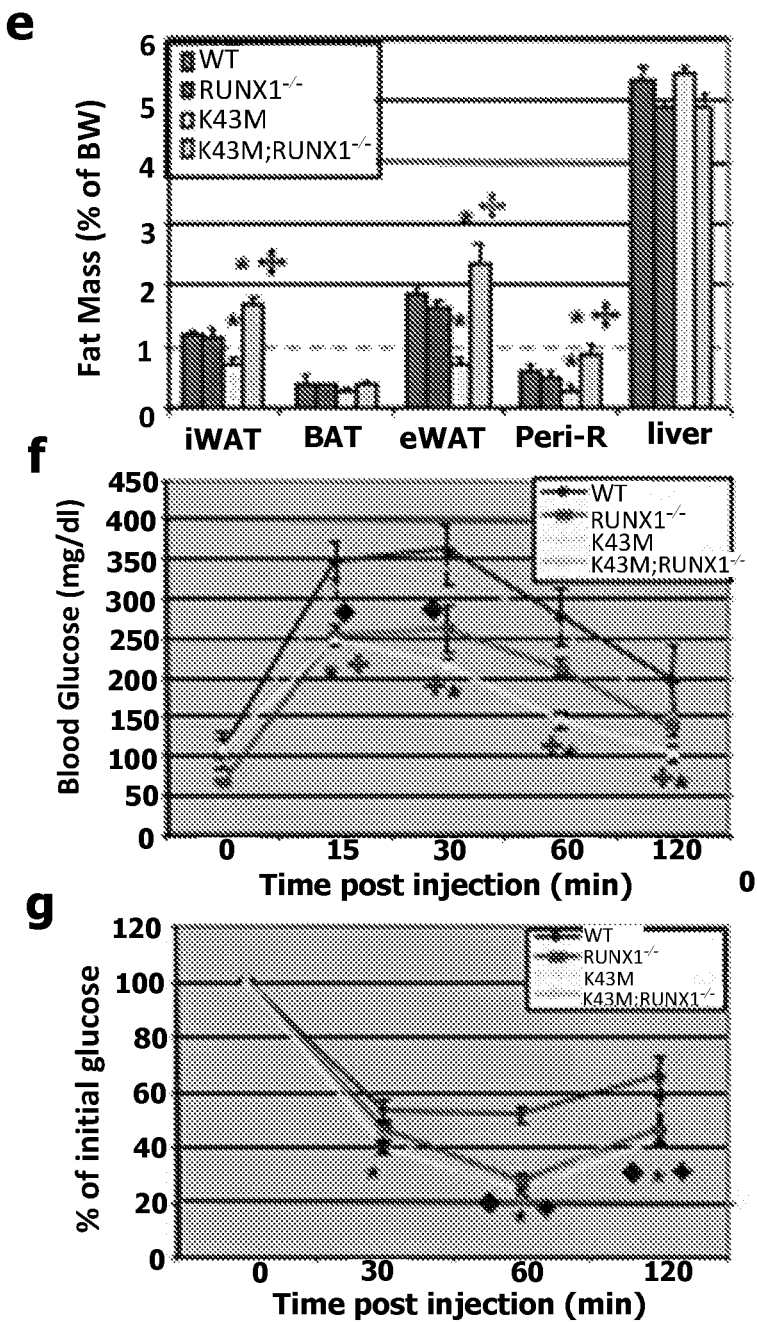
Figure 8:
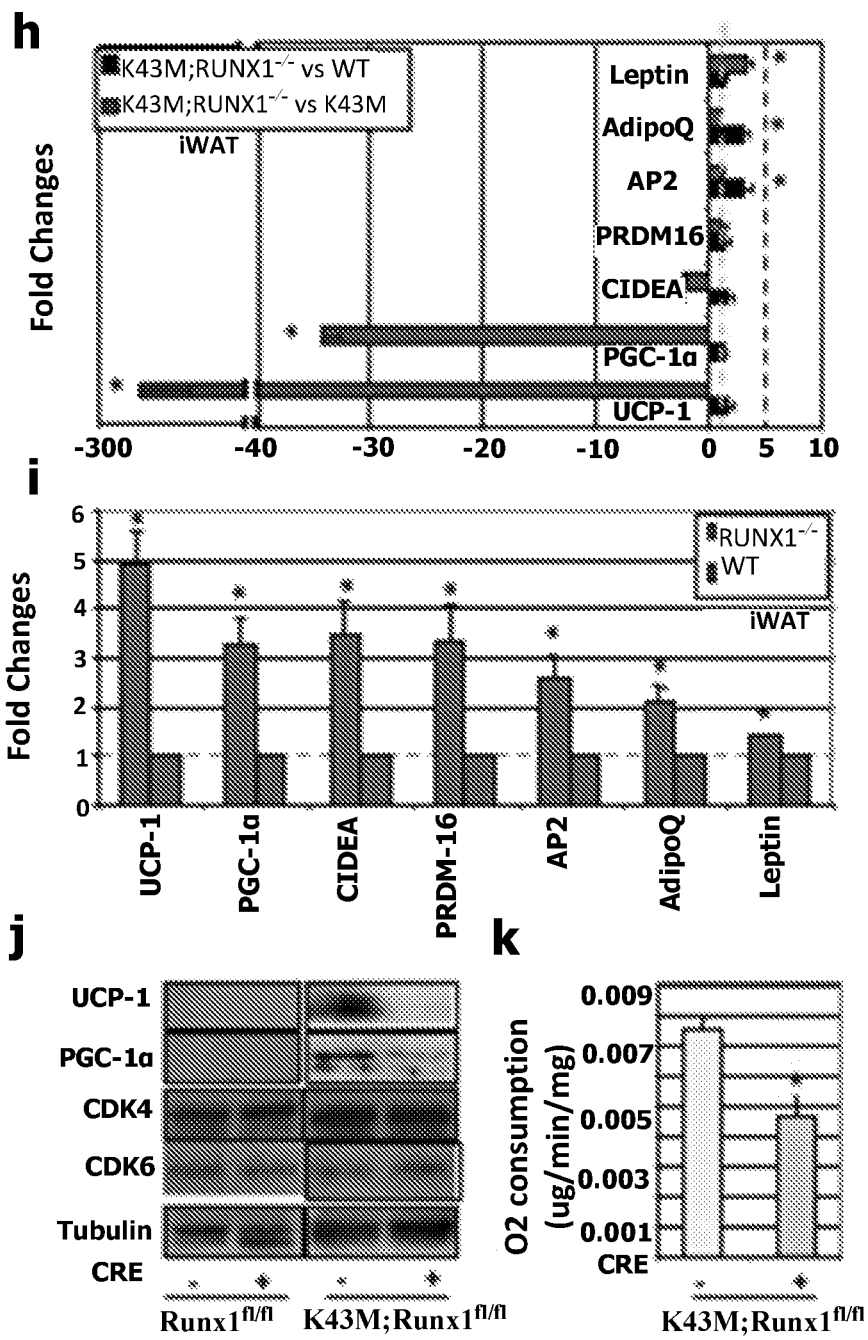

FIG. 8 shows that CDK6 inhibits white to beige fat transition by suppressing RUNX1. To further pinpoint the molecular mediator underlying the effect of CDK6 in white to beige fat transition, RUNX1 was investigated. An inverse relationship between CDK6 kinase activity and RUNX1 protein abundance (FIG. 3l, 6g) was observed. The over-abundance of RUNX1 in the absence of CDK6 protein or kinase activity may be due to reduced phosphorylation by CDK6, since phosphorylation of RUNX1 on serine 303 by CDK6 targets RUNX1 for degradation (Biggs, J. R., *Mol Cell Biol* 26, 7420-7429, 2006).

This inverse relationship in adipocytes prompted us to pursue if RUNX1, a known downstream substrate of CDK6 in vivo, serves as a downstream effector of CDK6 in the negative regulation of white fat browning. To this end, K43M; Runx1$^{fl/fl}$ mice were generated and Runx1$^{fl/fl}$ and K43M; Runx1$^{fl/fl}$ were crossed with Adipoq-Cre mice to carry out the specific deletion of RUNX1 in mature adipocytes. The presence of DNA recombination of Cdk6 alleles (Hu, M. G., et al. *Blood* 117, 6120-6131, 2011), Cre expression, WT-Runx1 alleles and Floxed-Runx1 alleles, and deleted Floxed-Runx1 alleles were confirmed by PCR (Chen, M. J., et al. *Nature* 457, 887-891, 2009) in adipocytes of the resultant mice.

K43M; Runx$^{-/-}$ mice gained significantly more body weight than K43M mice (data not shown) under NCD. Loss of Runx1 in the K43M background reversed white fat browning (FIG. 8a-d), enhanced fat masses (FIG. 8e), and reduced glucose tolerance (FIG. 8f), but had no effect on insulin sensitivity (FIG. 8g).

Consistent with observed phenotypes, K43M; Runx1$^{-/-}$ mice had reduced expression of BAT-specific genes and increased WAT-specific gene leptin (FIG. 8h), reduced expression of BAT-specific proteins in iWAT (FIG. 8j), and reduced $O_2$ consumption (FIG. 8k), which may partially explain why the ablation of Runx1 on K43M background reversed the phenotypes observed in K43M mice. The comparable expression levels of BAT-specific genes but increased expression of AdipoQ and Ap2 (FIG. 8h) may in part explain why K43M; Runx1$^{-/-}$ mice have greater fat pad masses than WT mice. Similarly, ablation of Runx1 on WT background also led to increased BAT-specific genes in iWAT (FIG. 8i). However, these increases are countered at least in part by increased WAT-specific genes in iWAT (FIG. 8i), thus maintaining the homeostasis of WAT development. Together, these data indicated that RUNX1 mediated the effects of K43M on the regulation of white fat browning and glucose metabolism but not insulin sensitivity.

Example 2

This Example describes inhibition of CDK6 by CDK4/6 inhibitors (PD0332991 and LEE011) can induce brown-like adipocytes in vitro, which further demonstrates that CDK6 kinase activity is required for negatively regulating white fat browning in a cell-autonomous manner, and as such represents a target for therapeutic intervention of obesity and related metabolic diseases.

Figure 10:
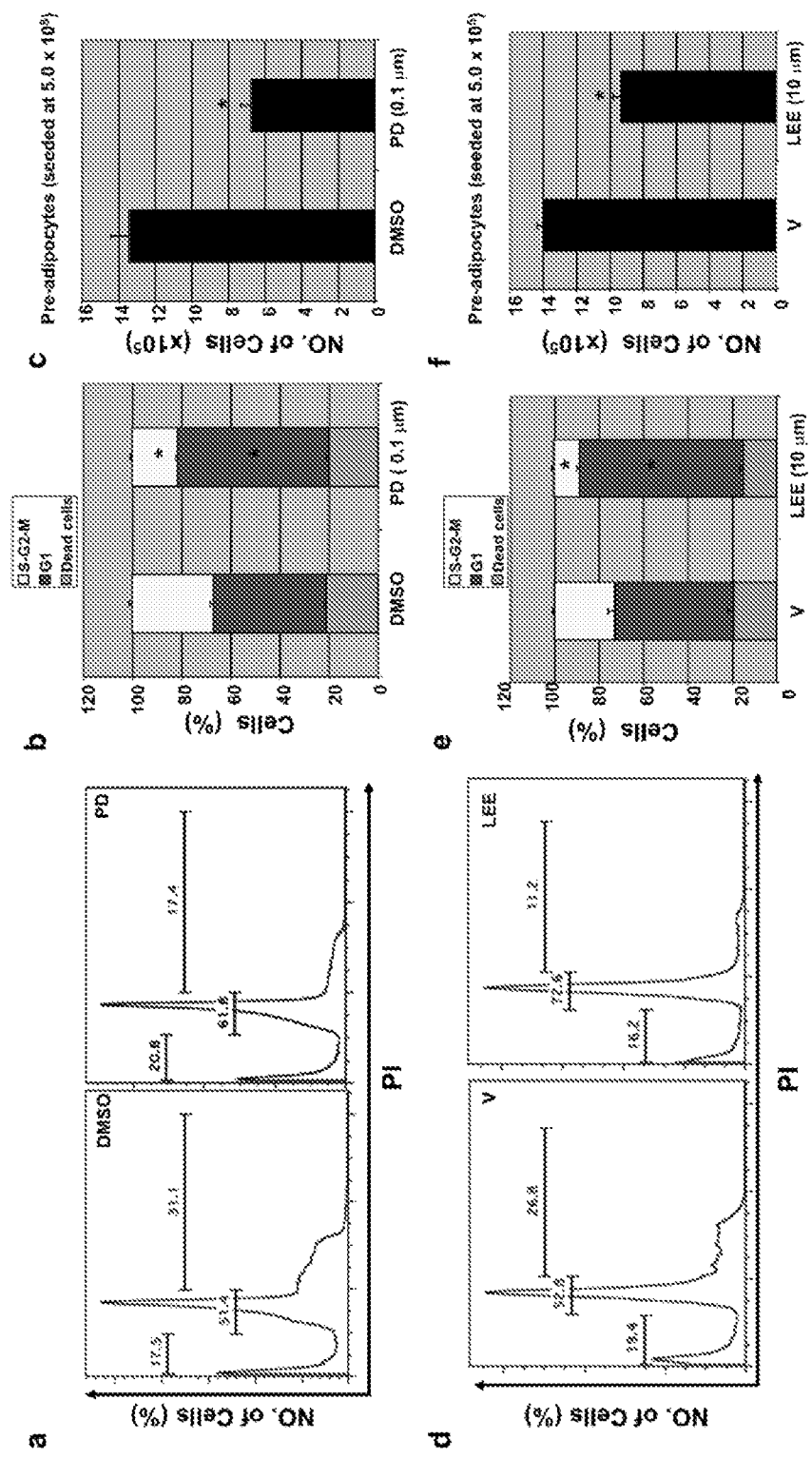
FIG. 10 shows that WT-ADSCs cells are sensitive to CDK4/6 inhibitors. (a, d) representative flow cytometric cell cycle profiles of WT-ADSCs cells treated with either PD (0.1 μM) or LEE (10 μM) for 6 days. (b, e) histograms summarizing the cell cycle distribution of the cells in A and D. Data shown are mean±s.d. (n=6); *P<0.05 vs DMSO or V, t-test. (c, f) Histograms summarizing the total cell numbers in WT-ADSCs cells treated with DMSO or PD (0.1 μM) for 6 days (c), or WT-ADSCs cells treated with vehicle (0.5% methycellulose) or LEE for 6 days (F). Data shown are mean±s.d. (n=6); *P<0.05 vs DMSO or V, t-test. The initial plating cells were 5×10$^5$.

FIG. 10 shows that inhibition of CDK4/6 kinase activity impairs the ability of WT-ADSCs cells to proliferate and induces cell cycle arrest. Given the central role of CDK6 as a negative regulator in white fat browning in vivo described above, the findings were extended to additional therapeutically relevant models. It was determined if inhibition of CDK4/6 kinase activity has similar effect in white fat browning as ablation of CDK6 kinase activity in the mice.

To accomplish this, the anti-proliferation efficacy of CDK4/6 inhibitors against primary adipose derived stem cells (ADSCs) from the stromal vascular fraction (SVF) of WT adipose tissue (WT-ADSCs) we assessed. WT-ADSCs were treated with two known commercial available CDK4/6 inhibitors PD0332991 (PD) and LEE011 (LEE), two clinically relevant small molecule inhibitors of CDK4 and CDK6 kinases (Rader, J., et al. Clin Cancer Res 19, 6173-6182, 2013); Fry, D. W., et al. Mol Cancer Ther 3, 1427-1438, 2004; Pikman, Y., et al. Clin Cancer Res 23, 1012-1024, 2017) for 6 days with commonly used relevant effective doses (Fry, D. W., et al. Mol Cancer Ther 3, 1427-1438, 2004; Pikman, Y., et al. Clin Cancer Res 23, 1012-1024, 2017).

After treatment, WT-ADSCs had a dramatic reduction in the frequency of proliferating cells (FIG. 10 *a, b, d,* and *e,* S-G2-M), accompanied with the increased frequency of quiescence cells (G1). Consistently, the total cell numbers (FIG. 10 *c, f*) were successfully reduced after treatment with both PD and LEE. Collectively, these results indicate that CDK4/6 kinase activity is required for growth and proliferation of ADSCs, as inhibition of CDK4/6 blocks cell proliferation, and induces cell cycle arrest.

Figure 11:
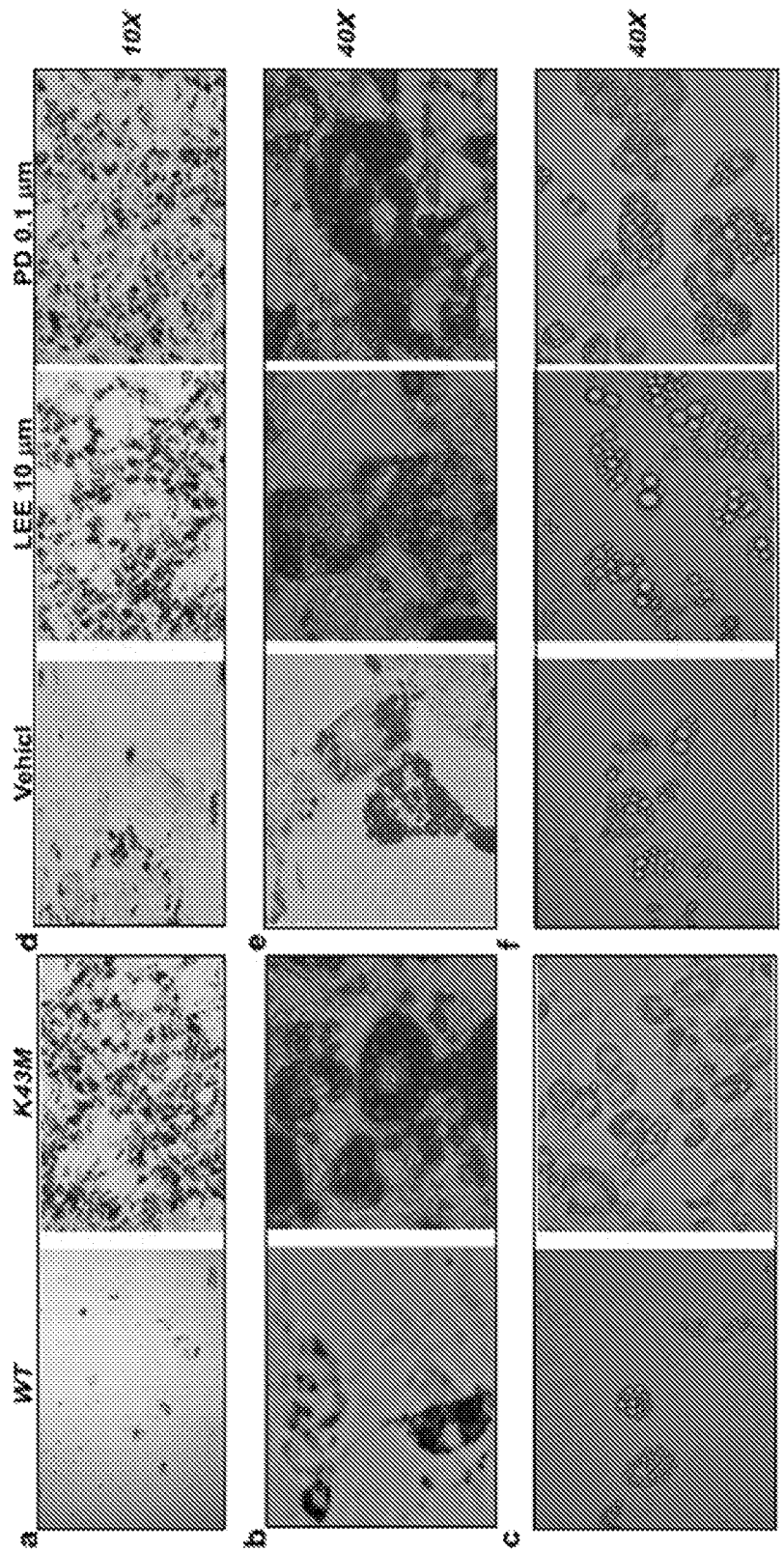
FIG. 11 shows that ADSCs of K43M mice or ADSCs treated with CDK4/6 inhibitors differentiated towards fat cells with characteristics of brown adipocytes. (a, d) Representative images of Oil Red O staining of differentiated ADSCs from WT and K43M mice (a, 10×) or WT-ADSCs treated with CDK4/6 inhibitor LEE011 (10 μM) and PD (0.1 μM) (a, 10×) in the presence of BAT inducers. (b, e) Representative images of Oil Red O staining of differentiated ADSCs from WT and K43M mice (b, 40×) or WT-ADSCs treated with CDK4/6 inhibitor LEE011 10 μM and PD 0.1 μM (e, 40×) in the presence of BAT inducers. (c, f) Representative images of bright field images of differentiated ADSCs from iWAT of WT and K43M mice or WT-ADSCs treated with CDK4/6 inhibitor LEE011 (10 μM) and PD (0.1 μM) (f, 40×) in the presence of BAT inducers.
Figure 12:
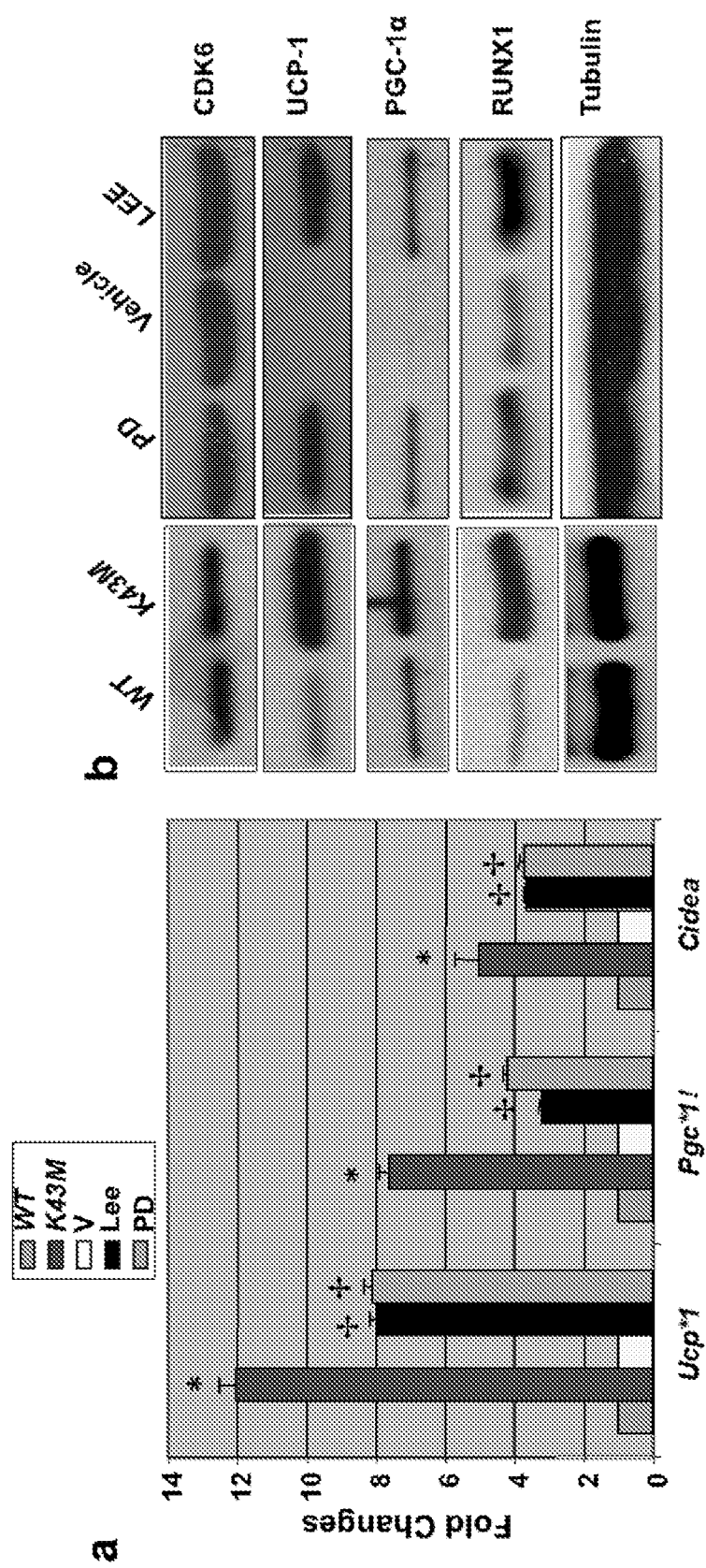
FIG. 12 shows that the absence of CDK6 kinase activity or inhibition of CDK4/6 kinase activity by two inhibitors enhanced BAT genes and protein expression in vitro. (a) Relative mRNA levels of BAT markers Ucp-1, Pgc-1α and Cidea in differentiated ADSCs in the presence of BAT inducers. Data shown are fold changes normalized to the relative WT/V controls, which was arbitrarily defined as 1 unit, *p<0.05, vs WT, t-test (n=6). $^+p$ <0.05, vs V, t-test (n=6). (b) lysates from cells were analyzed by immunoblotting for expression of CDK6, UCP-1, PGC-1α, and RUNX1. Tubulin was used as loading control.

FIGS. 11 and 12 show that ablation of CDK6 kinase activity or inhibition of CDK4/6 kinase activity by two small molecules promotes differentiation towards brown-like adipocytes in vitro. Cellular differentiation entails the coordination of cell cycle arrest and tissue-specific gene expression. The involvement of CDK6 in differentiation towards brown-like adipocytes was investigated in vitro using the mouse ADSCs derived from WT and K43M adipose tissue. ADSCs shares a number of similarities, although not identical, to bone marrow derived mesenchymal stem cells (BMSC), for instance, they contain large population of stem cells with multi-lineage differentiation capacity (Bunnell, B. A., et al. *Methods Mol Biol* 456, 155-171, 2008). In vitro, confluent primary ADSCs isolated from iWAT of WT or K43M mice were stimulated with brown fat inducers (Aune, U. L., et al. *J Vis Exp,* 73, e5019, 2013) for 7 days. As shown in FIG. 11, in the presence of BAT inducers, ADSCs derived from K43M mice turn into more brown-like adipocytes than those derived from WT mice (FIG. 11*b, c*). Accumulation of lipid-containing cells was detected by Oil red O staining as described (Hansen, J. B., et al. *J Biol Chem* 274, 2386-2393, 1999) (FIG. 11 *a-b*) and the characteristic feature of multilocular beige cells were also visualized under light microscopy (FIG. 11*c*). The critical adipogenic gene expression of BAT marker (FIG. 12*a*) and proteins (FIG. 12*b*) were significantly increased in K43M cells.

To test if inhibition of CDK6 kinase activity by CDK4/6 inhibitors mimics the loss of kinase activity in K43M-ADSCs, WT-ADSCs were treated with vehicle or inhibitor in the presence of BAT inducers. Similar to K43M-ADSCs cells, WT-ADSCs treated with both inhibitors have enhanced brown-like differentiation as evidenced by increased Oil red O staining, accompanied by increased expression of BAT specific markers (FIG. 11 *d-f,* 12*a-b*), compared with those cells treated with vehicle.

Together, these data indicate that the absence or inhibition of CDK4/6 kinase activity does restrict precursors from executing the adipogenic program under the influence of adipogenic factors, and CDK6 is important for negative regulation of white fat browning.

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled relevant fields are intended to be within the scope of the following claims.

I claim:

1. A method of treating metabolic disease in a subject diagnosed with a metabolic disease selected from the group consisting of type II diabetes, obesity, metabolic syndrome, elevated blood pressure, cardiovascular diseases, elevated fasting plasma glucose, and high serum triglycerides, comprising:
   administering a CDK6 inhibitor to said subject,
   wherein said administering reduces one or more symptoms of said metabolic disease.

2. The method of claim 1, wherein said CDK6 inhibitor is selected from the group consisting of a nucleic acid, a small molecule, a peptide, and an antibody.

3. The method of claim 2, wherein said CDK6 inhibitor is a small molecule.

4. The method of claim 3, wherein said small molecule is selected from the group consisting of PD0332991, LEE011, AT7519, JNJ-7706621, P276-00, and their pharmaceutically acceptable salts thereof.

5. The method of claim 1, wherein said administering converts white fat to brown fat in said subject.

6. The method of claim 1, wherein said subject is overweight or obese.

7. The method of claim 1, wherein said subject is not overweight or obese.

8. The method of claim 1, wherein said subject exhibits symptoms of said metabolic disease.

9. The method of claim 1, wherein said subject does not exhibit symptoms of said metabolic disease.

10. The method of claim 1, wherein said CDK6 inhibitor is administered in combination with a second agent that treats a metabolic disease.

11. A method of treating metabolic disease in a subject diagnosed with a metabolic disease selected from the group consisting of type II diabetes, obesity, metabolic syndrome, elevated blood pressure, cardiovascular diseases, elevated fasting plasma glucose, and high serum triglycerides, comprising:

administering a CDK6 inhibitor to said subject, wherein said CDK6 inhibitor is selected from the group consisting of PD0332991, LEE011, AT7519, JNJ-7706621, P276-00, and their pharmaceutically acceptable salts thereof, wherein said administering reduces one or more symptoms of said metabolic disease.

* * * * *

SEQUENCE LISTING

```
<160> NUMBER OF SEQ ID NOS: 1

<210> SEQ ID NO 1
<211> LENGTH: 11628
<212> TYPE: DNA
<213> ORGANISM: Homo sapiens

<400> SEQUENCE: 1
aacctctccg cgcgaagacg gcttcagccc tgcagggaaa gaaaagtgca atgattctgg      60
actgagacgc gcttgggcag aggctatgta atcgtgtctg tgttgaggac ttcgcttcga     120
ggagggaaga ggagggatcg gctcgctcct ccggcggcgg cggcggcggc gactctgcag     180
gcggagtttc gcggcggcgg caccagggtt acgccagccc cgcggggagg tctctccatc     240
cagcttctgc agcggcgaaa gccccagcgc ccgagcgcct gagccggcgg ggagcaagta     300
aagctagacc gatctccggg gagccccgga gtaggcgagc ggcggccgcc agctagttga     360
gcgcaccccc cgcccgcccc agcggcgccg cggcgggcgg cgtccaggcg gcatggagaa     420
```

```
ggacggcctg tgccgcgctg accagcagta cgaatgcgtg gcggagatcg gggagggcgc      480
ctatgggaag gtgttcaagg cccgcgactt gaagaacgga ggccgtttcg tggcgttgaa      540
gcgcgtgcgg gtgcagaccg gcgaggaggg catgccgctc tccaccatcc gcgaggtggc      600
ggtgctgagg cacctggaga ccttcgagca ccccaacgtg gtcaggttgt ttgatgtgtg      660
cacagtgtca cgaacagaca gagaaaccaa actaacttta gtgtttgaac atgtcgatca      720
agacttgacc acttacttgg ataaagttcc agagcctgga gtgcccactg aaaccataaa      780
ggatatgatg tttcagcttc tccgaggtct ggactttctt cattcacacc gagtagtgca      840
tcgcgatcta aaaccacaga acattctggt gaccagcagc ggacaaataa aactcgctga      900
cttcggcctt gcccgcatct atagtttcca gatggctcta acctcagtgg tcgtcacgct      960
gtggtacaga gcacccgaag tcttgctcca gtccagctac gccacccccg tggatctctg     1020
gagtgttggc tgcatatttg cagaaatgtt tcgtagaaag cctcttttc gtggaagttc     1080 agatgttgat caactaggaa aaatcttgga cgtgattgga ctcccaggag aagaagactg     1140
gcctagagat gttgcccttc ccaggcaggc ttttcattca aaatctgccc aaccaattga     1200
gaagtttgta acagatatcg atgaactagg caaagaccta cttctgaagt gtttgacatt     1260
taacccagcc aaaagaatat ctgcctacag tgccctgtct cacccatact tccaggacct     1320
ggaaaggtgc aaagaaaacc tggattccca cctgccgccc agccagaaca cctcggagct     1380
gaatacagcc tgaggcctca gcagccgcct aagctgatc ctgcggagaa cacccttggt     1440
ggcttatggg tccccctcag caagccctac agagctgtgg aggattgcta tctggaggcc     1500
ttccagctgc tgtcttctgg acaggctctg cttctccaag gaaaccgcct agtttactgt     1560
tttgaaatca atgcaagagt gattgcagct ttatgttcat ttgtttgttt gtttgtctgt     1620
ttgtttcaag aacctggaaa aattccagaa gaagagaagc tgctgaccaa ttgtgctgcc     1680
atttgatttt tctaaccttg aatgctgcca gtgtggagtg ggtaatccag cacagctga     1740 gttatgatgt aatctctctg cagctgccgg gcctgatttg gtacttttga gtgtgtgtgt     1800
gcatgtgtgt gtgtgtgtgt gtgtgtgtgt gtgtgtatgt gagagattct gtgatctttt     1860
aaagtgttac tttttgtaaa cgacaagaat aattcaattt taaagactca aggtggtcag     1920
taaataacag gcatttgttc actgaaggtg attcaccaaa atagtcttct caaattagaa     1980
agttaacccc atgtcctcag catttctttt ctggccaaaa gcagtaaatt tgctagcagt     2040
aaaagatgaa gttttataca cacagcaaaa aggagaaaaa attctagtat attttaagag     2100
atgtgcatgc attctattta gtcttcagaa tgctgaattt acttgttgta agtctatttt     2160
aaccttctgt atgacatcat gctttatcat ttcttttgga aaatagcctg taagcttttt     2220
attacttgct ataggtttag ggagtgtacc tcagatagat tttaaaaaaa agaatagaaa     2280
gcctttattt cctggtttga aattcctttc ttcccttttt ttgttgttgt tattgttgtt     2340
tgttgttgtt attttgtttt tgtttttagg aatttgtcag aaactctttc ctgttttggt     2400
ttggagagta gttctctcta actagagaca ggagtggcct tgaaattttc ctcatctatt     2460
acactgtact ttctgccaca cactgccttg ttggcaaagt atccatcttg tctatctccc     2520
ggcacttctg aaatatattg ctaccattgt ataactaata acagattgct taagctgttc     2580
ccatgcacca cctgtttgct tgctttcaat gaacctttca taaattcgca gtctcagctt     2640
atggtttatg gcctcgattc tgcaaaccta acagggtcac atatgttctc taatgcagtc     2700
cttctacctg gtgtttactt tgttaccta aataatgagt aggatcttgt tttgttttat     2760
```

```
caccagcaca cagattgcta taaactgtta ctttgtgaat tacattttta tagaagatat    2820
tttcagtgtc tttacctgag ggtatgtctt tagctatgtt ttagggccat acatttactc    2880
tatcaaatga tcttttctcc atcccccagg ctgtgcttat ttctagtgcc ttgtgctcac    2940
tcctgctctc tacagagcca gcctggcctg ggcattgtaa acagcttttc cttttctct    3000 tactgttttc tctacagtcc tttatatttc ataccatctc tgccttataa gtggtttagt    3060
gctcagttgg ctctagtaac cagaggacac agaaagtatc ttttggaaag tttagccacc    3120
tgtgctttct gactcagagt gcatgcaaca gttagatcat gcaacagtta gattatgttt    3180
agggttagga ttttcaaaga atggaggttg ctgcactcag aaaataattc agatcatgtt    3240
tatgcattat taagttgtac tgaattcttt gcagcttaat gtgatatatg actatcttga    3300
acaagagaaa aaactaggag atgtttctcc tgaagagctt ttggggttgg aactattct     3360 tttttaattg ctgtactact taacattgtt ctaattcagt agcttgagga acaggaacat    3420
tgttttctag agcaagataa taaggagat gggccataca aatgttttct actttcgttg     3480
tgacaacatt gattaggtgt tgtcagtact ataaatgctt gagatataat gaatccacag    3540
cattcaaggt caggtctact caaagtctca catggaaaag tgagttctgc ctttcctttg    3600
atcgagggtc aaaatacaaa gacattttg ctagggccta caaattgaat ttaaaaactc     3660
actgcactga ttcatctgag cttttggtt agtattcatg gctagagtga acatagcttt     3720 agttttgct gttgtaaaag tgtttttcata agttcactca agaaaatgc agctgttctg     3780 aactggaatt tttcagcatt ctttagaatt ttaaatgagt agagagctca actttattc     3840 ctagcatctg cttttgactc atttctaggc agtgcttatg aagaaaatt aaagcacaaa     3900 cattctggca ttcaatcgtt ggcagattat cttctgatga cacagaatga aagggcatct    3960
cagcctctct gaactttgta aaatctgtc cccagttctt ccatcggtgt agttgttgca     4020
tttgagtgaa tactctcttg atttatgtat tttatgtcca gattcgccat ttctgaaatc    4080
cagatccaac acaagcagtc ttgccgttag ggcattttga agcagatagt agagtaagaa    4140
cttagtgact acagcttatt cttctgtaac atatggtttc aaacatcttt gccaaaagct    4200
aagcagtggt gaactgaaaa gggcatattg ccccaaggtt acactgaagc agctcatagc    4260
aagttaaaat attgtgacag atttgaaatc atgtttgaat ttcatagtag gaccagtaca    4320
agaatgtccc tgctagtttc tgtttgatgt ttggttctgg cggctcaggc atttgggaa     4380 ctgttgcaca gggtggagtc aaaacaacct acatataaaa agagaaaaag agaaacttgt    4440
ccatttagct ttcataagaa atcccatggc aagggtaat aaaaaggacc taatcttaaa     4500
aatacaattt ctaagcactt gtaagaaccc agtgggttgg agcctccac tttgtccctc     4560 ctttgaagtg gatgggaact caaggtgcaa agaacctgtt ttggaagaaa gcttggggcc    4620
atttcagccc cctgtattct catgatttc tctcaggaag cacacactgt gaatggcaga     4680
cttttcattt agccccaggt gacttactaa aaatagttga aaattattca cctaagaata    4740
gaatctcagc attgtgttaa ataaaaatga aagcttaga aggcatgaga tgttcctatc     4800
ttaaataaag catgtttctt ttctatagag aaatgtatag tttgactctc cagaatgtac    4860
tatccatctt gatgagaaaa ctcttaaata gtaccaaaca ttttgaactt taaattatgt    4920
atttaaagtg agtgtttaag aaactgtagc tgcttctttt acaagtggtg cctattaaag    4980
tcagtaatgg ccattattgt tccattgtgg aaattaaatt atgtaagctt cctaatatca    5040
taaacatatt aaaattcttc taaaatattg cttttctttt aagtgacaat ttgactattc    5100
ttatgataag cacatgagag tgtcttacat tttccaaaag caggctttaa ttgcatagtt    5160
```

```
gagtctagga aaaaataatg ttaaaagtga atatgccacc ataattactt aattatgtta      5220
gtatagaaac tacagaatat ttaccctgga aagaaaatat tggaatgtta ttataaactc      5280
ttagatattt atataattca aaagaatgca tgtttcacat tgtgacagat aaagatgtat      5340
gatttctaag gctttaaaaa ttattcataa aacagtgggc aatagataaa ggaaattctg      5400
gagaaaatga aggtatttaa agggtagttt caaagctata tatattttga aggatatatt      5460
ctttatgaac aaatatattg taaaaattta tactaaggtc atctggtaac tgtgggatta      5520
atatggtcga aaacaaatgt tatggagaag ctgtcccaag caaactaaat tacctgtact      5580
tttttcccat ttcaagggaa gaggcaacca catgaagcaa tacttcttac acatgcctaa      5640
gaacgttcat tgaaaaaata aattttttaaa aggcatgtgt ttcctatgcc accaatactt     5700
ttgaaaaatt gtgaacctta cccaaaacca tttatcatgt ccattaagta tatttgggta      5760
tataattagg aagatattta catgttccat ctccacagtg gaaaaactta ttgaggctac      5820
caaagtgtgc caagaaatgt aagtccttag agtaattaga aatgctgttt tcctcaaaag      5880
catgagaaac tagcattttc atttcttatt tactccctt ctatatcaat gcaattcaca       5940
acccaatttt aatacatccc tatatctcaa gcatttctat cttgtacttt ttcagaaaat      6000
aaaccaaaaa taatcctttg gtctctctat cttctgacct ttgtaagcaa cagaaatgta     6060
aaaacagaag gggtccaatt tttacacgtt tttttctcaa gtagcctttc tggggatttt     6120
tattttctta atgaagtgcc aatcagcttt tcaaaatgtt ttctatttct cagcatttcc     6180
aggaagtgat aacgtttagc taaatgagta gaagtggact tccttcaaca tattgttacc    6240
ttgtctagcc ttaggaagaa aacaagagcc acctgaaaat aaatacaggc tcttttcgag    6300
catctgctga aatactgtta cagcaatttg aagttgatgt ggtaggaaag gaaggtgact    6360
tttcttgcaa aagtctttct aaacattcac actgtcctaa gagatgagct ttcttgtttt    6420
attccggtat attccacaag gtggcacttt tagagaaaaa caaatctgat gaagactaaa   6480
gaggtacttc taaaagagat ttcattctaa ctttatttttt ctgcgcatat ttaactcttt   6540
cctagcactt gttttttggg atgattaata gtctctataa tgttctgtaa cttcaatatt    6600
ttacttgtta cctaggttct gaacaattgt ctgcaaataa attgttctta aggatggata    6660
atacacccat tttgatcatt taagtaaaga aagcctagtc attcattcag tcaagaaaaa   6720
atttttgaag tacccagtta ccttactttt ctagattaaa acaggcttag ttactaaaaa   6780
ggcagtcctc atctgtgaac aggatagttt cgttagaagt ataaaactcc tttagtggcc   6840
ccagttaaaa cacacatacc ctctctgctg ctttcaaatt ccctagcatg gtggcctttc  6900
aacattgatt aaatttttaaa atcctaattt aaagatcagg tgagcaaaat gagtagcaca  6960
tcagtaattc agtagacaaa acttttgtct gaaaaattgc tgtattgaaa cagagcccta  7020
aaataccaaa agaccaggta atttttaacat ttgtggaatc acaaatgtaa attcataaga   7080
agctctaatt aaaaaaaaaa agtctgaagt atatgagcat aacaacttag gagtgtgtct   7140
acatacttaa cttttgaagt ttttttggcaa ctttatatac tttttttaaa tttacaagtc  7200
tacttaaaga cttcttatac cccaaatgat taagttaatt ttagaggtca cctttctcac   7260
agcagtgtca cttgaaattt agtagggaag gatattgcag tattttttcag tttccttagc  7320 acagcaccac agaaagcagc ttattccttt tgagtggcag acactcgacg gtgcctgccc  7380
aactttcctc ctgagtggca agcagatgag tctcagtaat tcatactgaa ccaaaatgcc  7440
acatacacta ggggcagtca gaaactggct gagaaatccc ccgcctcatt cgcccctctg  7500
```

```
ctcccaggaa ctagagtcca gttaaagccc ctatgcgaaa ggccgaattc caccccaggg      7560
tttgttataa cagtggccag tctgaacccc atttgctcgt gctcaaaact tgattcccac      7620
ttgaaagcct tccgggcgcg ctgcctcgtt gccccgcccc tttggcagga gagaggcagt      7680
gggcgaggcc gggctggggc cccgcctccc actcacctgc cggtgcctga aattatgtgc      7740
ggccccgcgg gctgctttcc gaggtcagag tgccctgctg ctgtctcaga ggcatctgtt      7800
ctgcaaatct taggaagaaa aatgtcccta gtagcaaacg ggtgtcttct gtgcataaat      7860
aagtacaaca caattctccg aaagttcggg taaaaagaga tgcggtagca gctgccctgt      7920
gtgaagctgt ctaccccgca tctctcaggc gctaagctca gttttttgttt ttgtttttgt      7980 tttttttaaag aaaagatgta taattgcagg aatttttttt tatttttta ttttccatca      8040 ttctatatat gtgatggtga aagatatgcc tggaaaagtt ttgttttgaa aagtttattt      8100
tctgcttcgt cttcagttgg caaaagctct caattcttta gcttccagtt tcttttctct      8160 cttttttcttt gttaggtaat taaaggtatg taaacaaatt atctcatgta gcagggatt       8220 ttcatgttga gaggaatctt ccgtgtgagt tgtttggtca cacaaataac cctttctcaa      8280
ttttaggagt ttggattgtc aaatgtaggt ttttctcaaa gggggcatat aactacatat      8340
tgactgccaa gaactatgac tgtagcacta atcagcacac atagagccac acaattattt      8400
aatttctaac tctctgtggt ccctagaaaa attccgttga tgtgcttagg ttaaagttct      8460
gaagataccc gttgtaccct tacttgaaag tttctaatct taagttttat gaaatgcaat      8520
aatatgtatc agctagcaat atttctgtga tcaccaacaa ctctcagttt gatcttaaag      8580
tctgaataat aaaacaaatc ccagcagtaa tacattctt aaacctcaca gtgcatgata       8640
tatcttttca ttctgatcct gtgtttgcaa aaatatacac atgtatatca tagttcctca      8700 cttttattc atttgttttc ctattacctg tagtaaatat attagttagt acatggaatt        8760
tatagcatca gctacccca ggaacagcac ctgacaggcg ggggattttt ttcaagttg         8820 ttctacattt gcataaatta tttctattat tattcatgta tgttatttat ttctgaatca      8880
cactagtcct gtgaaagtac aactgaaggc agaaagtgtt aggattttgc atctaatgtt      8940
cattatcatg gtattgatgg acctaagaaa ataaaaatta gactaagccc ccaaataagc      9000
tgcatgcatt tgtaacatga ttagtagatt tgaatatata gatgtagtat tttgggtatc      9060
taggtgtttt atcattatgt aaaggaatta agtaaagga cttttgtagtt gtttttatta      9120 aatatgcata tagtagagtg caaaaatata gcaaaaataa aaactaaagg tagaaaagca      9180
ttttagatat gccttaattt agaaactgtg ccaggtggcc ctcggaatag atgccaggca      9240
gagaccagtg cctgggtggt gcctcctctt gtctgccctc atgaagaagc ttccctcacg      9300
tgatgtagtg ccctcgtagg tgtcatgtgg agtagtggga acaggcagta ctgttgagag      9360
gagagcagtg tgagagtttt tctgtagaag cagaactgtc agcttgtgcc ttgaggcttc      9420
cagaacgtgt cagatggaga agtccaagtt tccatgcttc aggcaactta gctgtgtaca      9480
gaagcaatcc agtgtggtaa taaaaagcaa ggattgcctg tataattat tataaaataa        9540 aagggatttt aacaaccaac aattcccaac acctcaaaag cttgttgcat ttttttggtat     9600 ttgaggtttt tatctgaagg ttaaagggca agtgtttggt atagaagagc agtatgtgtt      9660
aagaaaagaa aaatattggt tcacgtagag tgcaaattag aactagaaag ttttatacga      9720
ttatcatttt gagatgtgtt aaagtaggtt ttcactgtaa aatgtattag tgttctgca       9780 ttgccatagg gcctggttaa aactttctct taggtttcag gaagactgtc acatacagta      9840
agcttttttc cttctgactt ataatagaaa atgttttgaa agtaaaaaaa aaaaatctaa      9900
```

```
tttggaaatt tgacttgtta gtttctgtgt ttgaaatcat ggttctagaa atgtagaaat    9960
tgtgtatatc agatactcat ctaggctgtg tgaaccagcc caagatgacc aacatcccca   10020
cacctctaca tctctgtccc ctgtatctct tcctttctac cactaaagtg ttccctgcta   10080
ccatcctggc ttgtccacat ggtgctctcc atcttcctcc acatcatgga ccacaggtgt   10140
gcctgtctag gcctggccac cactcccaac ttgacctagc cacattcatc tagagatggt   10200
tcctgatgct gggcacagac tgtgctcatg gcacccatta gaaatgcctc tagcatcttt   10260
gtatgcatct tgatttttaa accaagtcat tgtacagagc attcagtttt ggctgtggta   10320
ccaagagaaa aactaatcaa gaatataaac cacattccag gctgctgttt tctctccatc   10380
tacaggccac acttttactg tatttcttca tacttgaaat tcattctgct attttcatat   10440
cagggtacag acttataagg gtgcatgttc cttaaaggtg cataattatt cttattccgt   10500
ttgcttatat tgctacagaa tgctctgttt tggtgctttg agttctgcag acccaagaag   10560
cagtgtggaa attcactgcc tgggacacag tcttataaga atgttggcag gtgactttgt   10620
atcagatgtt gcttctcttt tctctgtaca cagattgaga gttaccacag tggcctgtcg   10680
ggtccaccct gtgggtgcag cacagctctc tgaaagcaag aaccttccta cctattctaa   10740 cgttttgcc ctctaagaaa aatggcctca ggtatggtat agacatagca agaggggaag   10800
ggctgtctca ctctagcaac catccctcca ttacacacag aaagccctct tgaagcaaaa   10860
gaagaagaaa gaaagaaagc ttatctctaa ggctactgtc ttcagaatgc tctgagctga   10920
atgctcttgc tcctttccca agaggcagat gaaaatatag ccagtttatc tataccttc   10980 ctatctgagg aggagaatag aaaagtaggg taaatatgta acgtaaaata tgtcattcaa   11040
ggaccaccaa aactttaagt accctatcat taaaaatctg gttttaaaag tagctcaagt   11100
aagggatgct ttgtgaccca gggtttctga agtcagatag ccattcttac ctgcccctta   11160
ctctgactta ttgggaaagg gagaactgca gtggtgtttc tgttgcagtg gcaaaggtaa   11220
catgtcagaa aattcagagg gttgcatacc aataatcctt tggaaactgg atgtcttact   11280
gggtgctaga atgaaaatgt aggtatttat tgtcagatga tgaagttcat tgtttttttc   11340
aaaattggtg ttgaaatatc actgtccaat gtgttcactt atgtgaaagc taaattgaat   11400
gaggcaaaaa gagcaaatag tttgtatatt tgtaatacct tttgtatttc ttacaataaa   11460
aatattggta gcaaataaaa ataataaaaa caataacttt aaactgcttt ctggagatga   11520
attactctcc tggctatttt cttttttact ttaatgtaaa atgagtataa ctgtagtgag   11580
taaaattcat taaattccaa gttttagcag aaaaaaaaaa aaaaaaaa                11628
```